United States Patent [19]

Nuebling et al.

[11] Patent Number: 5,190,963
[45] Date of Patent: Mar. 2, 1993

[54] CYCLOPROPANE(THIO)CARBOXAMIDES, THE PREPARATION THEREOF AND INTERMEDIATES THEREFOR, AND THE USE THEREOF FOR CONTROLLING PESTS

[75] Inventors: Christoph Nuebling, Hassloch; Hans Theobald, Limburgerhof; Uwe Kardorff, Mannheim; Wolfgang Krieg, Weingarten; Christoph Kuenast, Otterstadt, all of Fed. Rep. of Germany

[73] Assignee: BASF Aktiengesellschaft, Ludwigshafen, Fed. Rep. of Germany

[21] Appl. No.: 830,154

[22] Filed: Feb. 3, 1992

[30] Foreign Application Priority Data

Feb. 5, 1991 [DE] Fed. Rep. of Germany ....... 4103382

[51] Int. Cl.$^5$ .................. C07D 261/06; C07D 285/12; C07D 271/10; A01N 43/80; A01N 43/82
[52] U.S. Cl. ................................ 514/363; 514/364; 514/378; 514/380; 548/136; 548/138; 548/141; 548/143; 548/144; 548/145; 548/243; 548/244; 548/245; 548/246; 548/247
[58] Field of Search ............... 548/247, 136, 143, 243, 548/244, 245, 246, 138, 141, 144, 145; 514/378, 380, 363, 364

[56] References Cited

U.S. PATENT DOCUMENTS 4,859,706 8/1989 Buerstinghaus et al. ............ 514/624
5,013,847 5/1991 Leyendecker ...................... 548/378

FOREIGN PATENT DOCUMENTS 351617 7/1989 European Pat. Off. ............ 548/247
258733 8/1989 European Pat. Off. ............ 514/624
3841433 12/1988 Fed. Rep. of Germany ...... 548/247

OTHER PUBLICATIONS

CA 110(7): 57173c Preparation ... Pesticides, Neubauer et al., p. 641, 1989.

Primary Examiner—Mary C. Lee
Assistant Examiner—Joseph K. McKane
Attorney, Agent, or Firm—Keil & Weinkauf

[57] ABSTRACT

Cyclopropane(thio)carboxamides of the general formula I

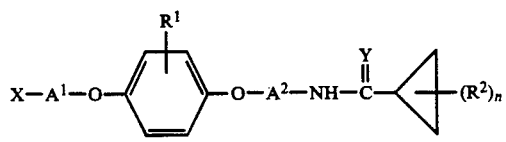

where the index and the substituents have the following meanings:
  n is 0, 1 or 2, it being possible for the $R^2$ radicals to be different when n is 2;
  $A^1$ and $A^2$ are substituted or unsubstituted alkylene;
  $R^1$ is hydrogen, halogen or alkyl;
  $R^2$ is halogen or alkyl;
  X is substituted or unsubstituted 5-membered heteroaryl, substituted or unsubstituted pyrazolyl-1-oxy or triazolyl-1-oxy; and
  Y is oxygen or sulfur, processes for their manufacture, intermediates therefor, and the use of compounds I.

6 Claims, No Drawings

CYCLOPROPANE(THIO)CARBOXAMIDES, THE PREPARATION THEREOF AND INTERMEDIATES THEREFOR, AND THE USE THEREOF FOR CONTROLLING PESTS

The present invention relates to cyclopropane(thio)carboxamides of the formula I

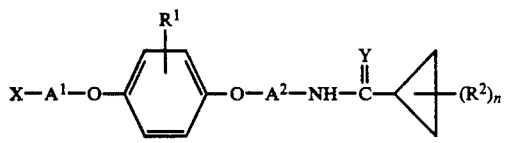

where n is 0, 1 or 2, it being possible for the $R^2$ radicals to be different when n is 2;

$A^1$ is methylene, ethylene or propylene, it being possible for these groups to carry one or two $C_1$-$C_3$-alkyl groups;

$A^2$ is ethylene or propylene, it being possible for these groups to carry one or two $C_1$-$C_3$-alkyl groups;

$R^1$ is hydrogen, halogen or $C_1$-$C_6$-alkyl;

$R^2$ is halogen or $C_1$-$C_3$-alkyl;

X is a 5-membered heteroaromatic radical which is bonded via carbon or nitrogen and contains from one to three nitrogens or one oxygen or one sulfur or contains one or two nitrogens and one oxygen or one sulfur as hetero atoms, or is 1-pyrazolyloxy or 1-triazolyloxy, it being possible for these 5-membered heteroaromatic rings to carry on their carbon atoms from one to three of the following: nitro, cyano, $C_1$-$C_6$-alkyl, $C_1$-$C_4$-haloalkyl, $C_1$-$C_6$-alkoxy, $C_1$-$C_4$-haloalkoxy, $C_1$-$C_4$-alkylthio, $C_1$-$C_4$-haloalkylthio, $C_1$-$C_4$-alkoxy-$C_1$-$C_4$-alkyl, $C_3$-$C_8$-cycloalkyl, $C_2$-$C_8$-alkenyl, $C_2$-$C_8$-alkynyl, aryl or aryl-$C_1$-$C_{10}$-alkyl, it being possible for the aromatic radicals in turn to carry from one to five halogens and/or one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

Y is oxygen or sulfur.

The present invention also relates to processes for preparing these compounds, to pesticides containing them and to methods for controlling pests.

The present invention additionally relates to intermediates for preparing the cyclopropane(thio)carboxamides I, namely phenols of the formula VIII

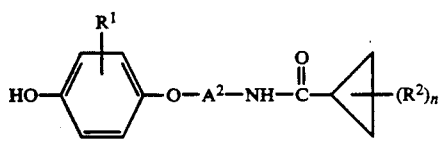

where n and $A^2$, $R^1$ and $R^2$ have the abovementioned meanings, and to amines of the formula X

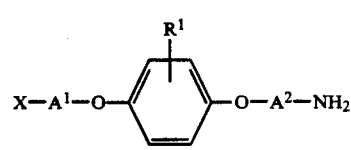

where $A^1$, $A^2$, $R^1$ and X have the abovementioned meanings.

Cyclopropanecarboxamides with a pesticidal action have been disclosed (N-phenoxyphenoxyalkylcyclopropanecarboxamides: EP-A 258,733, EP-A 350,688 and DE-A 3,841,433; N-alkoxyphenoxyalkylcyclopropanecarboxamides: EP-A 285,934; N-6-ring-heteroaryloxyphenoxyalkylcyclopropanecarboxamides: EP-A 351,617; cyclopropanethiocarboxamides: German Application 3,926,468), the action of which against pests is not always satisfactory, for example at low application rates.

It is an object of the present invention to find novel compounds suitable for controlling pests and processes for the preparation thereof and the use thereof.

We have found that this object is achieved by the cyclopropane(thio)carboxamides I defined in the introduction. We have also found processes and novel intermediates for preparing these cyclopropane(thio)carboxamides, pesticides containing them, and methods for the use thereof.

The cyclopropane(thio)carboxamides I can be obtained in a variety of ways.

Compounds of the formula I where Y is oxygen are obtained in a particularly advantageous manner by etherifying a 4-hydroxyphenyl ether of the formula II in a conventional manner in an inert organic solvent in the presence of a base with a nitrile of the formula III to give a hydroquinone diether of the formula IV, subsequently reducing the cyano group in a conventional manner, then converting the resulting primary amine of the formula V with an activated cyclopropanecarboxylic acid of the formula VI into the corresponding amide of the formula VII, liberating from VII, by cleaving the protective group R, the corresponding phenol of the formula VIII, and then esterifying the latter in a conventional manner with a heteroarylalkyl compound of the formula IX to give I.

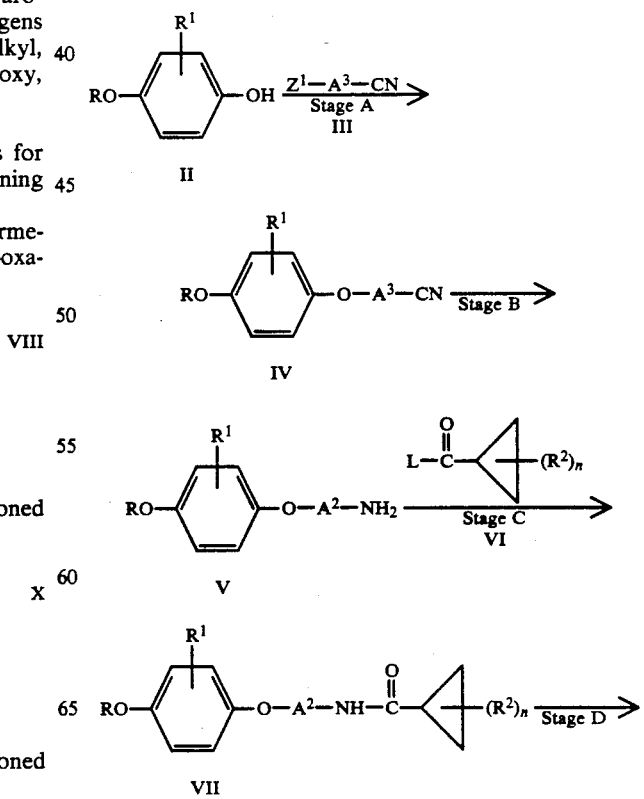

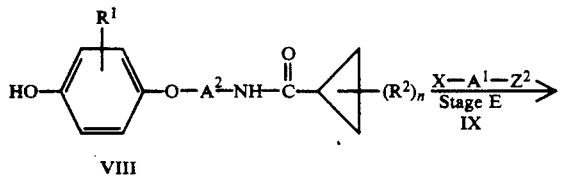

VIII

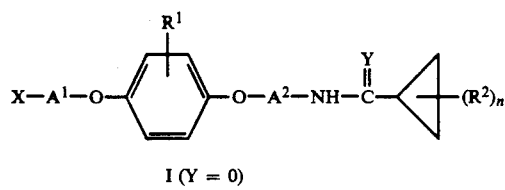

I (Y = 0)

R in the formulae II, IV, V and VII means a protective group which is inert under the reaction conditions, eg. $C_1-C_6$-alkyl such as pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-imethylbutyl, 1-ethylbutyl, 2-ethylbutyl, 1,1,2-trimethylpropyl, 1,2,2- trimethylpropyl, 1-ethyl-1-methylpropyl and 1-ethyl-2-methylpropyl, preferably $C_1-C_4$-alkyl such as methyl, ethyl, propyl, 1-methylethyl, butyl, 1-methylpropyl, 2-methylpropyl and 1,1-dimethylethyl, especially 1,1-dimethylethyl; benzyl which can carry on the phenyl ring from one to five halogens such as fluorine, chlorine, bromine and iodine, preferably fluorine, chlorine and bromine, and/or from one to three of the following: $C_1-C_4$-alkyl such as methyl, ethyl, propyl, 1-methylethyl, butyl, 1-methylpropyl, 2-methylpropyl and 1,1-dimethylethyl, preferably methyl, ethyl, propyl, 1-methylethyl and 1,1-dimethylethyl, especially methyl, ethyl and 1,1-dimethylethyl; $C_1-C_4$-alkoxy such as methoxy, ethoxy, propyloxy, 1-methylethoxy, butyloxy, 1-methylpropyloxy, 2-methylpropyloxy and 1,1-dimethylethoxy; silyl which is substituted three times by $C_1-C_6$-alkyl and/or unsubstituted or substituted phenyl as detailed above, especially trimethylsilyl, tert-butyldimethylsilyl, phenyldimethylsilyl and tert-butyldiphenylsilyl, $C_1-C_4$-alkoxy-$C_1-C_4$-alkyl such as methyl, ethyl, propyl, 1-methylethyl, butyl, 1-methylpropyl, 2-methylpropyl or 1,1-dimethylethyl, which is substituted in position 1 or 2 by methoxy, ethoxy, propyloxy, 1-methylethoxy, butyloxy, 1-methylpropyloxy, 2-methylpropyloxy or 1,1-dimethylethoxy, especially methoxymethyl, or $C_1-C_4$-alkoxyethoxy-$C_1-C_4$-alkyl such as methyl, ethyl, propyl, 1-methylethyl, butyl, 1-methylpropyl, 2-methylpropyl or 1,1-dimethylethyl, which is substituted in position 1 or 2 by methoxyethoxy, ethoxyethoxy, propyloxyethoxy, 1-methylethoxyethoxy, butyloxyethoxy, 1-methylpropyloxyethoxy, 2-methylpropyloxyethoxy or 1,1-dimethylethoxyethoxy, especially methoxyethoxymethyl.

$Z^1$ in the formula III and $Z^2$ in the formula IX are each, independently of one another, nucleofugic leaving groups, eg. halogen such as, in particular, chlorine, bromine and iodine, $C_1-C_4$-alkylsulfonyl such as methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl, especially methylsulfonyl; phenylsulfonyl which can carry on the phenyl ring from one to five halogens such as fluorine, chlorine, bromine and iodine, preferably fluorine, chlorine and bromine, and/or from one to three of the following: $C_1-C_4$-alkyl such as methyl, ethyl, propyl, 1-methylethyl, butyl, 1-methylpropyl, 2-methylpropyl and 1,1-dimethylethyl, preferably methyl, ethyl, propyl, 1-methylethyl and 1,1-dimethylethyl, especially methyl, ethyl and 1,1-dimethylethyl;

$A^3$ in the formula III is methylene or ethylene which can carry one or two $C_1-C_3$-alkyl radicals such as methyl, ethyl, propyl and 1-methylethyl, preferably methyl and ethyl, especially methyl.

L in the formula VI is a nucleophilically displaceable leaving group such as halogen, for example chlorine, bromine and iodine; $C_1-C_4$-alkyloxy such as methyloxy, ethyloxy, propyloxy, 1-methylethyloxy, butyloxy, 1-methylpropyloxy, 2-methylpropyloxy and 1,1-dimethylethyloxy, especially methyloxy and ethyloxy.

The specific procedures for the reactions are as follows:

Stage A: etherification (Houben-Weyl, Methoden der organischen Chemie, Vol. VI/3, pages 1 et seq., 49 et seq., Thieme Verlag, Stuttgart, 1965)

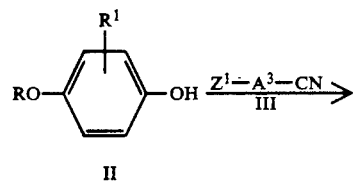

II

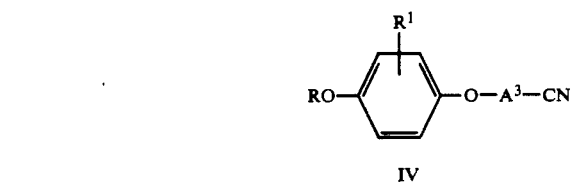

IV

The etherification is normally carried out at from $-20°$ to $170°$ C., preferably from $20°$ to $130°$ C.

The rate of the etherification is generally sufficient above $20°$ C. It is not as a rule necessary to exceed $130°$ C. for complete conversion. The reaction may evolve heat, for which reason it may be advantageous to provide means for cooling.

Generally suitable as bases are inorganic compounds such as alkali metal and alkaline earth metal hydroxides, for example lithium hydroxide, sodium hydroxide, potassium hydroxide and calcium hydroxide, alkali metal and alkaline earth metal oxides, for example lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates, for example lithium carbonate, sodium carbonate, potassium carbonate and calcium carbonate, alkali metal bicarbonates, for example sodium bicarbonate, organometallic compounds, especially alkali metal alkyls, for example methyllithium, butyllithium and phenyllithium, alkali metal and alkaline earth metal alcoholates, for example sodium methanolate, sodium ethanolate, potassium ethanolate, potassium tert-butanolate and dimethoxymagnesium, also organic bases, eg. tertiary amines such as trimethylamine, triethylamine, diisopropylethylamine and N-methylpiperidine, pyridine, substituted pyridines such as collidine, lutidine and 4-dimethylaminopyridine, and bicyclic amines. Potassium hydroxide, potassium carbonate, sodium methylate, sodium ethylate, potassium tert-butylate and sodium hydride are particularly preferred. Normally at least the equivalent amount of the base is used, but it can also be used in excess or, where appropriate, as solvent.

Examples of suitable solvents are aliphatic hydrocarbons such as pentane, hexane, yyclohexane and petroleum ether, aromatic hydrocarbons such as toluene, o-, m- and p-xylene, halohydrocarbons such as methylene chloride, ethylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol and isopropanol, and aprotic dipolar solvents such as dimethyl sulfoxide, dimethylformamide and pyridine, particularly preferably acetonitrile, ethanol and dimethylformamide.

It is also possible to use mixtures of the said solvents.

The starting materials are normally reacted together in stoichiometric amounts. It may be advantageous, for example to increase the yield, to use one of the starting materials in an excess of from 0.1 to 10 mol eq., preferably 0.2 to 1.5 mol eq.

Where $Z^1$ or $Z^2$ in one of the formulae III or VII is chlorine or bromine, the reaction rate can generally be increased by adding catalytic amounts of potassium iodide. The catalyst is normally used in amounts of from 5 to 20 mol %.

Stage B: reduction
(Organikum, 15th Edition, pages 540 et seq., 614 et seq., VEB Deutscher Verlag der Wissenschaften, Berlin 1977)

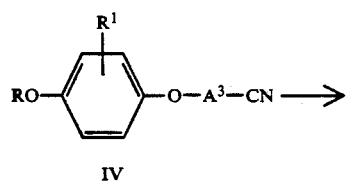

IV

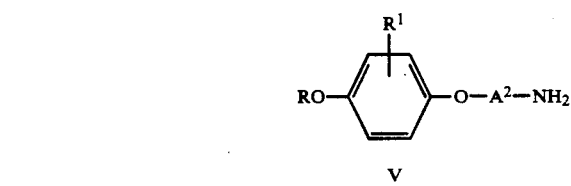

V

The reduction is normally carried out at from $-30°$ to $100°$ C., preferably from $0°$ to $80°$ C.

The reduction rate is generally sufficient above $0°$ C. It is not as a rule necessary to exceed $80°$ C. for complete conversion.

Generally suitable as reducing agents are complex hydrides such as lithium aluminum hydride and borohydride or elemental hydrogen in the presence of metal catalysts such as Raney nickel. Lithium aluminum hydride and hydrogen/Raney nickel are particularly preferred.

Normally at least the equivalent amount of the reducing agent is used, but it can also be used in excess.

Examples of suitable solvents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, alcohols such as methanol, ethanol and isopropanol, particularly preferably diethyl ether and tetrahydrofuran.

It is also possible to use mixtures of the said solvents.

Stage C: amide formation
(Organikum, 15th Edition, pages 511 et seq., VEB Deutscher Verlag der Wissenschaften, Berlin 1977)

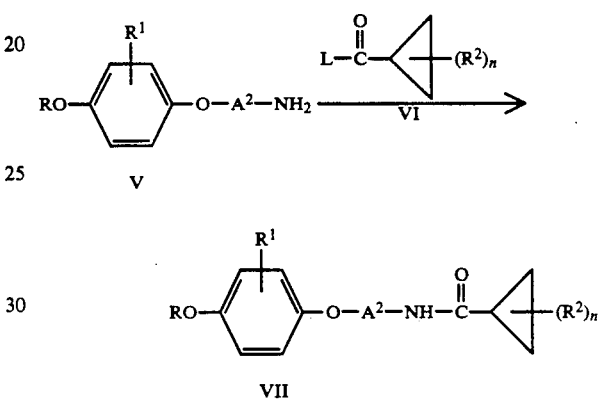

The amide formation is normally carried out at from $-20°$ to $100°$ C., preferably from $0°$ to $80°$ C.

The reaction rate is generally sufficient above $0°$ C. It is not as a rule necessary to exceed $80°$ C. for complete conversion.

Examples of suitable solvents are aliphatic hydrocarbons such as pentane, hexane, cyclohexane and petroleum ether, aromatic hydrocarbons such as toluene, o-, m- and p-xylene, halohydrocarbons such as methylene chloride, ethylene chloride, chloroform and chlorobenzene, ethers such as diethyl ether, diisopropyl ether, tert-butyl methyl ether, dioxane, anisole and tetrahydrofuran, alcohols such as methanol, ethanol and isopropanol, and aprotic dipolar solvents such as pyridine, particularly preferably diethyl ether, tetrahydrofuran and methylene chloride.

It is also possible to use mixtures of the said solvents.

Stage D: ether cleavage
(Houben-Weyl, Methoden der organischen Chemie, Vol. VI/1c, pages 314 et seq., Thieme Verlag, Stuttgart, 1976)

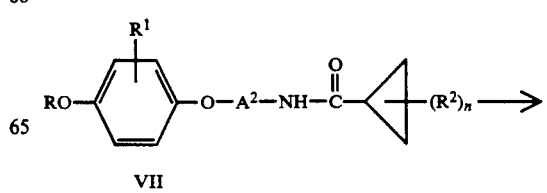

VII

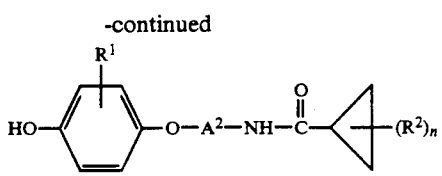

VIII

The protective group H is cleaved from the compound VII likewise in a conventional manner in a solvent in the presence of an acid or of an acidic catalyst.

The ethers VII are generally cleaved at from −20° to 120° C., preferably 20° to 100° C.

Suitable solvents for the cleavage are those mentioned above for the etherification, especially methanol, ethanol, chloroform and dioxane and mixtures thereof.

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid. The acids are generally employed in catalytic amounts but can also be used in equimolar amounts, in excess or, where appropriate, as solvent.

Stage E: etherification

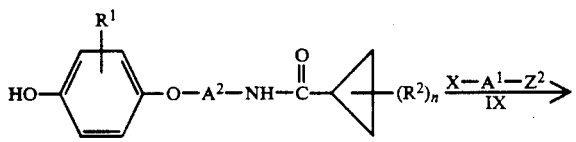

VIII

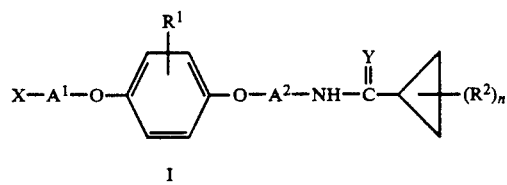

I

The etherification of the compounds VIII to give the products I is generally carried out under the conditions described for Stage A.

The compounds of the formula I where Y is sulfur are advantageously obtained by reacting a cyclopropanecarboxamide of the formula I where Y is oxygen in a conventional manner in an inert organic solvent in the presence of a sulfur-transferring reagent.

A suitable sulfur-transferring reagent is $P_4S_{10}$ or Lawesson's reagent [2,4-bis(4-methoxyphenyl)-1,3-dithia-2,4-diphosphetane 2,4-disulfide]. Reactions of this type are described in Houben-Weyl, Methoden der organischen Chemie, Vol. E5, pages 1242 et seq., Thieme Verlag, Stuttgart 1985. The thiation is generally carried out at from 0 to 150° C, preferably 50 to 120° C.

Examples of suitable solvents are aliphatic hydrocarbons such as petroleum ether, aromatic hydrocarbons such as toluene and xylenes, halohydrocarbons, ethers such as dioxane, anisole, glycol dimethyl ether and diglycol dimethyl ether, and aromatic amines such as pyridine, especially toluene, glycol dimethyl ether and pyridine.

The compounds I are also obtained, for example, by reacting an amine of the formula X in a conventional manner in an inert organic solvent with an activated cyclopropane(thio)carboxylic acid of the formula VI'.

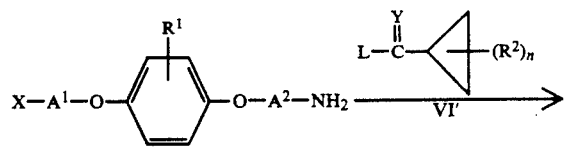

X

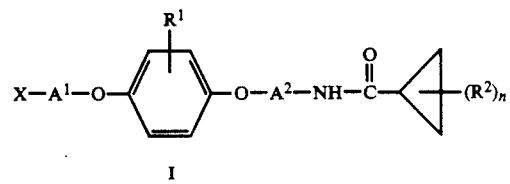

I

L in the formula VI' is a nucleophilically displaceable leaving group. Particularly suitable as nucleophilic leaving group in cases where Y is oxygen is halogen such as fluorine, chlorine, bromine or iodine, preferably chlorine and bromine, and alkoxy, preferably $C_1$-$C_4$-alkoxy such as methoxy, ethoxy, propyloxy, 1-methylethoxy, butyloxy, 1-methylpropyloxy, 2-methylpropyloxy and 1,1-dimethylethoxy, especially methoxy and ethoxy.

Particularly suitable as nucleophilic leaving group in cases where Y is sulfur is alkylthio, preferably $C_1$-$C_4$-alkylthio such as methylthio, ethylthio, propylthio, 1-methylethylthio, butylthio, 1-methylpropylthio, 2-methylpropylthio and 1,1-dimethylethylthio, especially methylthio and ethylthio.

The amide formation is normally carried out at from −50° to 150° C., preferably from −20° to 120° C.

The rate of amide formation is generally sufficient above −20° C. It is not as a rule necessary to exceed 120° C. for complete conversion. The reaction may evolve heat, for which reason it may be advantageous to provide a means for cooling.

Examples of suitable solvents are aliphatic hydrocarbons such as pentane, hexane, cyclohexane and petroleum ether, aromatic hydrocarbons such as toluene, o-, m- and p-xylene, halohydrocarbons such as methylene chloride, ethylene chloride, chloroform and chlorobenzene, ethers such as diethyl ether, diisopropyl ether, tert-butyl methyl ether, dioxane, anisole and tetrahydrofuran, alcohols such as methanol, ethanol and isopropanol, and aprotic dipolar solvents such as pyridine, particularly preferably diethyl ether, tetrahydrofuran and methylene chloride.

It is also possible to use mixtures of the said solvents.

The starting materials are normally reacted together in stoichiometric amounts. It may be advantageous, for example to increase the yield, to use one of the starting materials in an excess of from 0.1 to 10 mol eq., preferably 0.2 to 1.5 mol eq.

The amines of the formula X required for this process are obtained by reacting the 4-hydroxyphenyl ethers of the formula II with a heteroarylalkyl compound of the formula IX to give a diether of the formula V', cleaving the protective group, etherifying the resulting phenol of the formula VIII' with a nitrile of the formula III to give a hydroquinone diether of the formula IV' and subsequently reducing the cyano group.

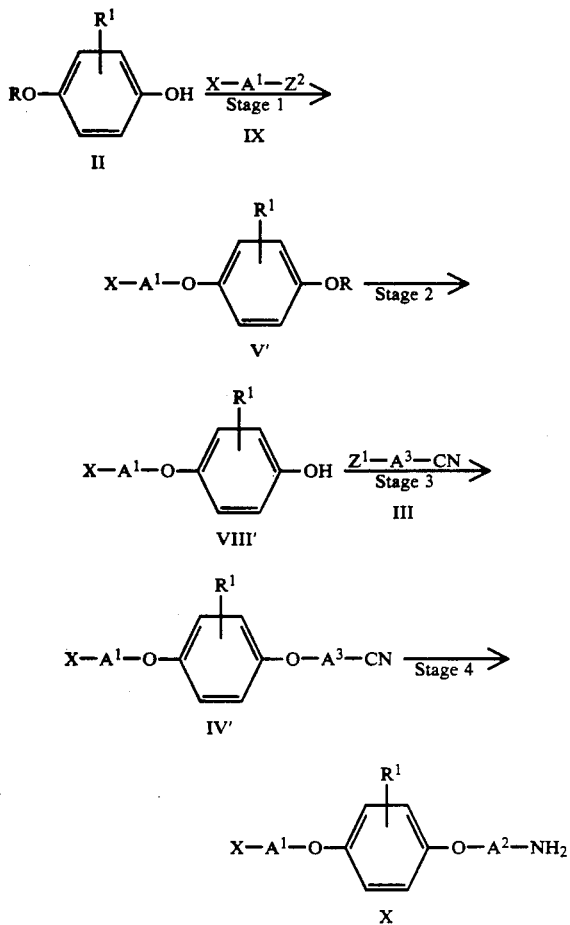

Stage 1: etherification

The etherification of the compounds II to give the diethers of the formula V' is generally carried out under the conditions described for Stage A.

Stage 2: ether cleavage

The cleavage of the compounds V' to give the phenols of the formula VIII' is generally carried out under the conditions described for Stage D.

Stage 3: etherification

The etherification of the compounds VIII' to give the diethers of the formula IV' is generally carried out under the conditions described for Stage A.

Stage 4: reduction

The reduction of the compounds IV' to give the amines X is generally carried out under the conditions described for Stage B.

The reaction mixtures are worked up in a conventional manner, eg. by mixing with water, separating the phases and, where appropriate, purifying the crude products by chromatography. The intermediates and final products are in some cases obtained as colorless or pale brown viscous oils which are purified by removing volatiles under reduced pressure and at moderately elevated temperature. Those intermediates and final products obtained as solids can be purified by recrystallization or digestion.

The hetarylalkyl derivatives of the formula IX required for the reaction are either known or commercially available or can be prepared by conventional processes.

Processes for preparing thiophene derivatives are to be found, for example, in Comprehensive Heterocyclic Chemistry, A. R. Katritzky and C. W. Rees, Vol. 4, pages 863 et seq., Pergamon Press 1984; thioazole, oxazole, isothiazole, thiadiazole and oxadiazole derivatives eg. in Comprehensive Heterocyclic Chemistry, A. R. Katritzky and C. W. Rees, Vol. 6, pages 131, 177, 235, 365, 427, 545 et seq., Pergamon Press 1984; imidazole derivatives eg in Advances in Heterocyclic Chemistry, Vol. 27 (1980) 242 et seq., pyrazole and triazole derivatives eg. in Comprehensive Heterocyclic Chemistry, A. R. Katritzky and C. W. Rees, Vol. 5, pages 167, 733 et seq., Pergamon Press 1984; isoxazole derivatives eg. in DE-A 2,549,962 and DE-A 2,754,832.

N-Methylazoles are in some cases disclosed in Heterocycles 24 (1986) 2233-2237 or can be obtained by the method described therein by reacting the azole with paraformaldehyde.

N-Hydroxypyrazoles are described, for example, in DE-A 3,820,738 and DE-A 3,820,739, and N-hydroxytriazoles are described, for example, in DE-A 3,900,347 or can be prepared by the processes described therein.

With a view to the intended use of the cyclopropane(-thio)carboxamides I in pesticides, suitable meanings are as follows:

n is 0, 1 or 2, it being possible for the $R^2$ radicals to be different when n is 2, preferably 0.

$A^1$ is methylene, ethylene or propylene, preferably methylene or ethylene, especially methylene, it being possible for these groups to carry one or two $C_1$-$C_3$-alkyl radicals such as methyl, ethyl, propyl and 1-methylethyl, preferably methyl and ethyl, especially methyl;

$A^2$ is ethylene or propylene, it being possible for these groups to carry one or two $C_1$-$C_3$-alkyl radicals such as methyl, ethyl, propyl and 1-methylethyl, preferably methyl and ethyl, especially methyl;

$R^1$ is hydrogen, halogen such as fluorine, chlorine, bromine and iodine, preferably fluorine, chlorine and bromine, especially fluorine and chlorine, or $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl-1,3-dimethylbutyl,2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_1$-$C_3$-alkyl, especially methyl and ethyl;

$R^2$ is halogen such as fluorine, chlorine, bromine and iodine, preferably fluorine, chlorine and bromine, especially fluorine and chlorine, or $C_1$-$C_3$-alkyl such as methyl, ethyl, propyl and 1-methylethyl, preferably methyl and ethyl, especially methyl;

X is a 5-membered heteroaromatic radical which is bonded via carbon or nitrogen and contains from one to three nitrogens or one oxygen or one sulfur or contains one or two nitrogens and one oxygen or one sulfur as hetero atoms, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 1-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-1-yl, 1,2,4-triazol-4-yl, 1,3,4-oxadiazol-2-yl, 1,3,4-thiadiazol-2-yl and 1,3,4-triazol-2-yl, preferably a heteroaromatic radical containing one or two nitrogens and/or one oxygen or sulfur as hetero atoms, especially 1-imidazolyl, 3-isoxazolyl, 5-isoxazolyl, 1,3,4-oxadiazol-2-yl and 1,3,4-thiadiazol-2-yl;

1-pyrazolyloxy or 1-triazolyloxy, it being possible for these 5-membered heteroaromatic rings to carry on their carbon atoms from one to three of the following: nitro, cyano, halogen such as fluorine, chlorine, bromine and iodine, preferably fluorine, chlorine and bromine, especially fluorine and chlorine;

$C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl-1,1,2-trimethylpropyl,1,2,2-trimethylpropyl, 1-ethyl-1-methylpropyl and 1-ethyl-2-methylpropyl, preferably $C_1$-$C_4$-alkyl, especially methyl, ethyl and propyl;

$C_1$-$C_4$-haloalkyl, especially $C_1$-$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, especially trifluoromethyl;

$C_1$-$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 1,1-dimethylpropyloxy, 1,2-dimethylpropyloxy, 2,2-dimethylpropyloxy, 1-ethylpropyloxy, hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy, preferably $C_1$-$C_3$-alkoxy, especially methoxy and ethoxy;

$C_1$-$C_4$-haloalkoxy, especially $C_1$-$C_2$-haloalkyloxy such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy, especially trifluoromethoxy and difluoromethoxy;

$C_1$-$C_4$-alkylthio such as methylthio, ethylthio, propylthio, 1-methylethylthio, butylthio, 1-methylpropylthio, 2-methylpropylthio and 1,1-dimethylethylthio, preferably $C_1$-$C_2$-alkylthio, especially methylthio;

$C_1$-$C_4$-haloalkylthio, especially $C_1$-$C_2$-haloalkylthio such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio, especially trifluoromethylthio;

$C_1$-$C_4$-alkyl as mentioned above which is substituted preferably in position 1 or 2 by $C_1$-$C_4$-alkoxy as mentioned above, eg. methoxymethyl, ethoxymethyl, propyloxymethyl, 1-methylethoxymethyl, methoxy-1-ethyl, ethoxy-1-ethyl, propyloxy-1-ethyl, 1-methylethoxy-1-ethyl, methoxy-2-ethyl, ethoxy-2-ethyl, propyloxy-2-ethyl, 1-methylethoxy-2-ethyl, methoxy-1-propyl, ethoxy-1-propyl, propyloxy-1-propyl, 1-methylethoxy-1-propyl, methoxy-2-propyl, ethoxy-2-propyl, propyloxy-2-propyl, 1-methylethoxy-2-propyl, methoxy-3-propyl, ethoxy-3-propyl, propyloxy-3-propyl, 1-methylethoxy-3-propyl, preferably $C_1$-$C_2$-alkoxy-$C_1$-$C_2$-alkyl, especially methoxymethyl, ethoxymethyl and methoxyethyl;

$C_3$-$C_8$-cycloalkyl such as cyclopropyl, cyclobutyl, cyclopentyl, cyclohexyl, cycloheptyl and cyclooctyl, especially cyclopropyl;

$C_2$-$C_8$-alkenyl, especially $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-1-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, preferably $C_2$-$C_4$-alkenyl, especially ethenyl, 1-propenyl and 2-propenyl;

$C_2$-$C_8$-alkynyl, especially $C_2$-$C_6$-alkynyl such as 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1- dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably $C_2$-$C_3$-alkynyl, especially ethynyl and 1-propynyl;

aryl such as phenyl, 1-naphthyl and 2-naphthyl, preferably phenyl, or $C_1$-$C_{10}$-alkyl substituted by aryl as mentioned above, especially $C_1$-$C_6$-alkyl as mentioned above, preferably $C_1$-$C_4$-alkyl as mentioned above, especially methyl, ethyl and propyl, it being possible for the aromatic radicals in turn to carry from one to five halogens such as fluorine, chlorine, bromine and iodine, preferably fluorine, chlorine and bromine, especially fluorine and chlorine, and/or from one to three of the following: $C_1$-$C_4$-alkyl such as methyl, ethyl, propyl, 1-methylethyl, butyl, 1-methylpropyl, 2-methylpropyl and 1,1-dimethylethyl, preferably $C_1$-$C_3$-alkyl, especially methyl and ethyl;

$C_1$-$C_4$-haloalkyl, especially $C_1$-$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, especially trifluoromethyl;

$C_1$-$C_4$-alkoxy such as methyloxy, ethyloxy, propyloxy, 1-methylethyloxy, butyloxy, 1-methylpropyloxy, 2-methylpropyloxy and 1,1-dimethylethyloxy, preferably $C_1$-$C_3$-alkoxy, especially methoxy and ethoxy;

$C_1$-$C_4$-haloalkoxy, especially $C_1$-$C_2$-haloalkyloxy such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy, especially difluoromethoxy and trifluoromethoxy;

$C_1$-$C_4$-alkylthio such as methylthio, ethylthio, propylthio, 1-methylethylthio, butylthio, 1-methylpropylthio, 2-methylpropylthio and 1,1-dimethylethylthio, preferably $C_1$-$C_3$-alkylthio, especially methylthio and ethylthio;

or $C_1$-$C_4$-haloalkylthio, especially $C_1$-$C_2$-haloalkylthio such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio, especially trifluoromethylthio;

Y is oxygen or sulfur.

Particularly preferred cyclopropane(thio)carboxamides of the formula I are those where $A^1$ is methylene, ethylene or propylene, it being possible for these groups to carry one or two methyl groups.

Particularly preferred cyclopropane(thio)carboxamides of the formula I are also those where $A^2$ is ethylene or propylene, it being possible for these groups to carry one or two methyl groups.

Also preferred cyclopropane(thio)carboxamides of the formula I are those where $R^1$ is hydrogen, fluorine, chlorine, bromine or methyl.

Likewise preferred cyclopropane(thio)carboxamides of the formula I are those where $R^2$ is fluorine, chlorine and/or methyl.

Additionally preferred cyclopropane(thio)carboxamides of the formula I are those where X is one of the following rings X-1 to X-32. The possible substituents on these rings have not been depicted for clarity; the linkage to $A^1$ is represented by .-.

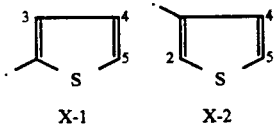

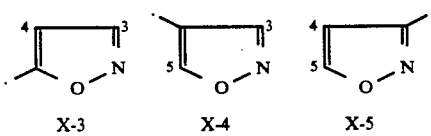

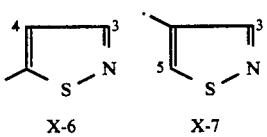

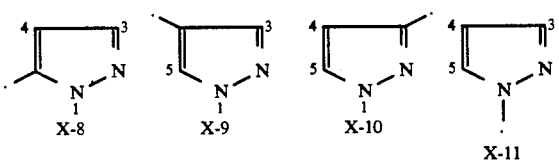

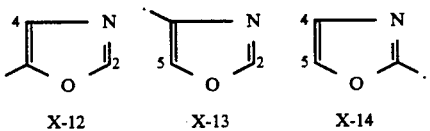

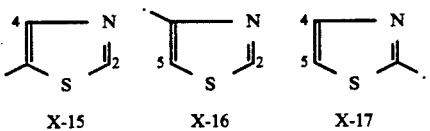

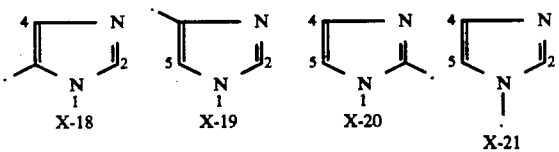

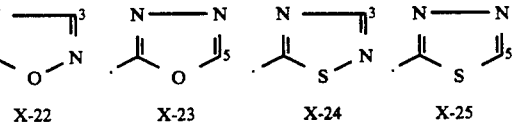

-continued

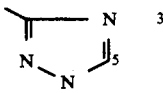
X-26

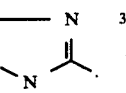
X-27

X-28

X-29

X-30

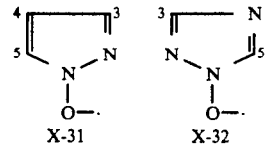
X-31    X-32

Examples of particularly preferred compounds of the general formula I are listed in the following table:

TABLE 1

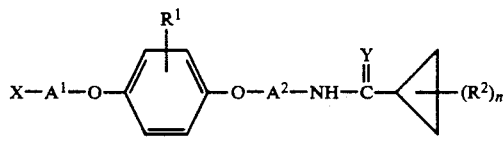

| X | Substituent on X | A¹ | R¹ | A² | (R²)ₙ | Y |
|---|---|---|---|---|---|---|
| X-1 | — | CH₂ | H | CH₂CH₂ | H | O |
| X-1 | — | CH(CH₃) | H | CH₂CH₂ | H | O |
| X-1 | — | CH(CH₂CH₃) | H | CH₂CH₂ | H | O |
| X-1 | — | CH₂ | 3-F | CH₂CH₂ | H | O |
| X-1 | — | CH₂CH₂ | H | CH₂CH₂ | H | O |
| X-1 | — | CH₂ | H | CH₂(CH₃)CH₂ | H | O |
| X-1 | — | CH₂ | H | CH₂CH₂CH₂ | H | O |
| X-1 | 5-CH₃ | CH₂ | H | CH₂CH₂ | H | O |
| X-1 | 4-CH₃ | CH₂ | H | CH₂CH₂ | H | O |
| X-1 | 3-CH₃ | CH₂ | H | CH₂CH₂ | H | O |
| X-1 | 5-Cl | CH₂ | H | CH₂CH₂ | H | O |
| X-1 | 5-Br | CH₂ | H | CH₂CH₂ | H | O |
| X-1 | 4-Cl | CH₂ | H | CH₂CH₂ | H | O |
| X-1 | 4-Br | CH₂ | H | CH₂CH₂ | H | O |
| X-1 | 5-Cyclopropyl | CH₂ | H | CH₂CH₂ | H | O |
| X-1 | 4-Cyclopropyl | CH₂ | H | CH₂CH₂ | H | O |
| X-1 | 4,5-Dichloro | CH₂ | H | CH₂CH₂ | H | O |
| X-1 | 5-Br | CH₂ | H | CH₂CH₂ | 1-CH₃ | O |
| X-1 | 5-Br | CH₂ | H | CH₂CH₂ | 2-CH₃ | O |
| X-1 | 4,5-Dichloro | CH₂ | 3-F | CH(CH₃)CH₂ | 2-CH₃ | O |
| X-1 | 5-Br | CH₂ | H | CH₂CH₂CH₂ | 1-CH₃ | O |
| X-1 | — | CH₂ | H | CH₂CH₂ | H | S |
| X-1 | — | CH(CH₃) | H | CH₂CH₂ | H | S |
| X-1 | — | CH(CH₂CH₃) | H | CH₂CH₂ | H | S |
| X-1 | — | CH₂ | 3-F | CH₂CH₂ | H | S |
| X-1 | — | CH₂CH₂ | H | CH₂CH₂ | H | S |
| X-1 | — | CH₂ | H | CH(CH₃)CH₂ | H | S |
| X-1 | — | CH₂ | H | CH₂CH₂CH₂ | H | S |
| X-1 | 5-CH₃ | CH₂ | H | CH₂CH₂ | H | S |
| X-1 | 4-CH₃ | CH₂ | H | CH₂CH₂ | H | S |
| X-1 | 3-CH₃ | CH₂ | H | CH₂CH₂ | H | S |
| X-1 | 5-Cl | CH₂ | H | CH₂CH₂ | H | S |
| X-1 | 5-Br | CH₂ | H | CH₂CH₂ | H | S |
| X-1 | 4-Cl | CH₂ | H | CH₂CH₂ | H | S |
| X-1 | 4-Br | CH₂ | H | CH₂CH₂ | H | S |
| X-1 | 5-Cyclopropyl | CH₂ | H | CH₂CH₂ | H | S |
| X-1 | 4-Cyclopropyl | CH₂ | H | CH₂CH₂ | H | S |
| X-1 | 4,5-Dichloro | CH₂ | H | CH₂CH₂ | H | S |
| X-1 | 5-Br | CH₂ | H | CH₂CH₂ | 1-CH₃ | S |
| X-1 | 5-Br | CH₂ | H | CH₂CH₂ | 2-CH₃ | S |
| X-1 | 4,5-Dichloro | CH₂ | 3-F | CH(CH₃)CH₂ | 2-CH₃ | S |
| X-1 | 5-Br | CH₂ | H | CH₂CH₂CH₂ | 1-CH₃ | S |
| X-2 | — | CH₂ | H | CH₂CH₂ | H | O |
| X-2 | 4-Cyclopropyl | CH₂ | H | CH₂CH₂ | H | O |
| X-2 | 5-Cyclopropyl | CH(CH₃) | H | CH(CH₃)CH₂ | H | O |
| X-2 | 5-Br | CH₂ | H | CH₂CH₂ | H | O |
| X-2 | 4,5-Dichloro | CH₂CH₂ | H | CH₂CH₂CH₂ | H | O |
| X-2 | 4,5-Dibromo | CH₂ | 3-F | CH₂CH₂ | H | O |
| X-2 | 5-Br | CH(CH₂CH₃) | H | CH₂CH₂ | 1-CH₃ | O |
| X-2 | 5-Br | CH₂ | H | CH(CH₃)CH₂ | 2-CH₃ | O |
| X-2 | 4-Cl | CH₂ | 3-F | CH(CH₃)CH₂ | 2,2-Cl₂ | O |
| X-2 | 5-Cyclopropyl | CH₂ | H | CH₂CH₂ | H | O |
| X-2 | 4-Cyclopropyl | CH₂CH₂ | H | CH₂CH₂CH₂ | H | O |
| X-2 | — | CH₂ | H | CH₂CH₂ | H | S |
| X-2 | 4-Cyclopropyl | CH₂ | H | CH₂CH₂ | H | S |

TABLE 1-continued

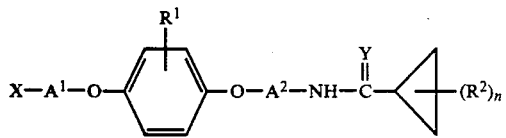

| X | Substituent on X | $A^1$ | $R^1$ | $A^2$ | $(R^2)_n$ | Y |
|---|---|---|---|---|---|---|
| X-2 | 5-Cyclopropyl | $CH(CH_3)$ | H | $CH(CH_3)CH_2$ | H | S |
| X-2 | 5-Br | $CH_2$ | H | $CH_2CH_2$ | H | S |
| X-2 | 4,5-Dichloro | $CH_2CH_2$ | H | $CH_2CH_2CH_2$ | H | S |
| X-2 | 4,5-Dibromo | $CH_2$ | 3-F | $CH_2CH_2$ | H | S |
| X-2 | 5-Br | $CH(CH_2CH_3)$ | H | $CH_2CH_2$ | H | S |
| X-2 | 5-Br | $CH_2$ | H | $CH(CH_3)CH_2$ | 1-$CH_3$ | S |
| X-2 | 4-Cl | $CH_2$ | 3-F | $CH(CH_3)CH_2$ | 2,2-$Cl_2$ | S |
| X-2 | 5-Cyclopropyl | $CH_2$ | H | $CH_2CH_2$ | H | S |
| X-2 | 4-Cyclopropyl | $CH_2CH_2$ | H | $CH_2CH_2CH_2$ | H | S |
| X-3 | 3-$CH_3$ | $CH_2$ | H | $CH_2CH_2$ | H | O |
| X-3 | 3-$CH_2CH_3$ | $CH_2$ | H | $CH_2CH_2$ | H | O |
| X-3 | 3-$CH(CH_3)_2$ | $CH_2$ | H | $CH_2CH_2$ | H | O |
| X-3 | 3-Cyclopropyl | $CH_2$ | H | $CH_2CH_2$ | H | O |
| X-3 | 3-$OCH_2CH_3$ | $CH_2$ | H | $CH_2CH_2$ | H | O |
| X-3 | 3-$CH_2OCH_3$ | $CH_2$ | H | $CH_2CH_2$ | H | O |
| X-3 | 3-$CF_3$ | $CH_2$ | H | $CH_2CH_2$ | H | O |
| X-3 | 3-$CH_3$ | $CH_2$ | H | $CH_2CH_2$ | 1-$CH_3$ | O |
| X-3 | 3-Cyclopropyl | $CH_2$ | H | $CH_2CH_2$ | 2-$CH_3$ | O |
| X-3 | 3-$CH(CH_3)_2$ | $CH_2$ | H | $CH_2CH_2$ | 1-$CH_3$ | O |
| X-3 | 3-$CH_3$ | $CH_2$ | H | $CH(CH_3)CH_2CH_2$ | H | O |
| X-3 | 3-Cyclopropyl | $CH_2CH_2CH_2$ | H | $CH_2CH_2$ | 2-$CH_3$ | O |
| X-3 | 3-$CF_3$ | $CH_2CH_2$ | 3-F | $CH_2CH_2$ | H | O |
| X-3 | 3-$OCH_2CH_3$ | $CH(CH_3)$ | H | $CH(CH_3)CH_2$ | H | O |
| X-3 | 3-$CH_2CH_3$ | $CH_2$ | 3-$CH_3$ | $CH_2CH_2$ | H | O |
| X-3 | 3-$CH_3$ | $CH_2$ | H | $CH_2CH_2$ | H | S |
| X-3 | 3-$CH_2CH_3$ | $CH_2$ | H | $CH_2CH_2$ | H | S |
| X-3 | 3-$CH(CH_3)_2$ | $CH_2$ | H | $CH_2CH_2$ | H | S |
| X-3 | 3-Cyclopropyl | $CH_2$ | H | $CH_2CH_2$ | H | S |
| X-3 | 3-$OCH_2CH_3$ | $CH_2$ | H | $CH_2CH_2$ | H | S |
| X-3 | 3-$CH_2OCH_3$ | $CH_2$ | H | $CH_2CH_2$ | H | S |
| X-3 | 3-$CF_3$ | $CH_2$ | H | $CH_2CH_2$ | H | S |
| X-3 | 3-$CH_3$ | $CH_2$ | H | $CH_2CH_2$ | 1-$CH_3$ | S |
| X-3 | 3-Cyclopropyl | $CH_2$ | H | $CH_2CH_2$ | 2-$CH_3$ | S |
| X-3 | 3-$CH(CH_3)_2$ | $CH_2$ | H | $CH_2CH_2$ | 1-$CH_3$ | S |
| X-3 | 3-$CH_3$ | $CH_2$ | H | $CH(CH_3)CH_2CH_2$ | H | S |
| X-3 | 3-Cyclopropyl | $CH_2CH_2CH_2$ | H | $CH_2CH_2$ | 2-$CH_3$ | S |
| X-3 | 3-$CF_3$ | $CH_2CH_2$ | 3-F | $CH_2CH_2$ | H | S |
| X-3 | 3-$OCH_2CH_3$ | $CH(CH_3)$ | H | $CH(CH_3)CH_2$ | H | S |
| X-3 | 3-$CH_2CH_3$ | $CH_2$ | 3-$CH_3$ | $CH_2CH_2$ | H | S |
| X-4 | — | $CH_2$ | H | $CH_2CH_2$ | H | O |
| X-4 | 5-$CH_3$ | $CH_2$ | H | $CH_2CH_2$ | H | O |
| X-4 | 3-$CH_3$ | $CH_2$ | H | $CH_2CH_2$ | H | O |
| X-4 | 3-$CH(CH_3)_2$ | $CH_2$ | H | $CH_2CH_2$ | H | O |
| X-4 | 3-$OCH_2CH_3$ | $CH(CH_3)$ | H | $CH(CH_3)CH_2$ | H | O |
| X-4 | 5-$OCH_2CH_3$ | $CH_2$ | 3-F | $CH(CH_3)CH_2$ | H | O |
| X-4 | 5-$CH(CH_3)_2$ | $CH_2CH_2$ | H | $CH_2CH_2CH_2$ | H | O |
| X-4 | — | $CH_2$ | H | $CH_2CH_2$ | H | S |
| X-4 | 5-$CH_3$ | $CH_2$ | H | $CH_2CH_2$ | H | S |
| X-4 | 3-$CH_3$ | $CH_2$ | H | $CH_2CH_2$ | H | S |
| X-4 | 3-$CH(CH_3)_2$ | $CH_2$ | H | $CH_2CH_2$ | H | S |
| X-4 | 3-$OCH_2CH_3$ | $CH(CH_3)$ | H | $CH(CH_3)CH_2$ | H | S |
| X-4 | 5-$OCH_2CH_3$ | $CH_2$ | 3-F | $CH(CH_3)CH_2$ | H | S |
| X-4 | 5-$CH(CH_3)_2$ | $CH_2CH_2$ | H | $CH_2CH_2CH_2$ | H | S |
| X-5 | — | $CH_2$ | H | $CH_2CH_2$ | H | O |
| X-5 | 5-$CH_3$ | $CH_2$ | H | $CH_2CH_2$ | H | O |
| X-5 | 5-Cyclopropyl | $CH_2$ | H | $CH_2CH_2$ | H | O |
| X-5 | 5-$OCH_2CH_3$ | $CH_2CH_2$ | H | $CH_2CH_2$ | H | O |
| X-5 | 5-Cyclopropyl | $CH(CH_3)$ | H | $CH_2CH_2$ | 1-$CH_3$ | O |
| X-5 | 5-Cyclopropyl | $CH_2$ | H | $CH(CH_3)CH_2$ | H | O |
| X-5 | 5-$CH_3$ | $CH(CH_3)$ | 3-F | $CH_2CH_2$ | 2-$CH_3$ | O |
| X-5 | 5-$CH_3$ | $CH_2CH_2CH_2$ | H | $CH_2CH_2CH_2$ | H | O |
| X-5 | 5-$OCH_2CH_3$ | $CH_2$ | H | $CH_2CH_2$ | 2,2-$Cl_2$ | O |
| X-5 | — | $CH_2$ | H | $CH_2CH_2$ | H | S |
| X-5 | 5-$CH_3$ | $CH_2$ | H | $CH_2CH_2$ | H | S |
| X-5 | 5-Cyclopropyl | $CH_2$ | H | $CH_2CH_2$ | H | S |
| X-5 | 5-$OCH_2CH_3$ | $CH_2CH_2$ | H | $CH_2CH_2$ | H | S |
| X-5 | 5-Cyclopropyl | $CH(CH_3)$ | H | $CH_2CH_2$ | 1-$CH_3$ | S |
| X-5 | 5-Cyclopropyl | $CH_2$ | H | $CH(CH_3)CH_2$ | H | S |
| X-5 | 5-$CH_3$ | $CH(CH_3)$ | 3-F | $CH_2CH_2$ | 2-$CH_3$ | S |
| X-5 | 5-$CH_3$ | $CH_2CH_2CH_2$ | H | $CH_2CH_2CH_2$ | H | S |
| X-5 | 5-$OCH_2CH_3$ | $CH_2$ | H | $CH_2CH_2$ | 2,2-$Cl_2$ | S |
| X-6 | — | $CH_2$ | 3-F | $CH_2CH_2$ | H | O |
| X-6 | 3-$CH_3$ | $CH_2$ | H | $CH_2CH_2$ | H | O |

TABLE 1-continued

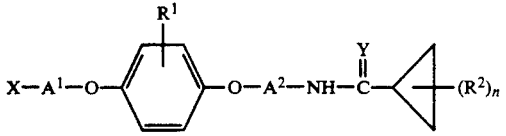

| X | Substituent on X | $A^1$ | $R^1$ | $A^2$ | $(R^2)_n$ | Y |
|---|---|---|---|---|---|---|
| X-6 | 3-Cyclopropyl | $CH_2$ | H | $CH_2CH_2$ | H | O |
| X-6 | 3-$OCH_2CH_3$ | $CH_2$ | H | $CH_2CH_2$ | H | O |
| X-6 | 3-Cyclopropyl | $CH(CH_3)$ | H | $CH(CH_3)CH_2$ | 1-$CH_3$ | O |
| X-6 | 3-Cyclopropyl | $CH_2$ | H | $CH_2CH_2CH_2$ | H | O |
| X-6 | 3-$CH_3$ | $CH_2CH_2$ | H | $CH_2CH_2$ | H | O |
| X-6 | 3-$CH_3$ | $CH_2$ | 3-$CH_3$ | $CH_2CH_2$ | 2,2-$Cl_2$ | O |
| X-6 | 3-Cyclopropyl | $CH_2$ | H | $CH(CH_3)CH_2$ | H | O |
| X-6 | — | $CH_2$ | 3-F | $CH_2CH_2$ | H | S |
| X-6 | 3-$CH_3$ | $CH_2$ | H | $CH_2CH_2$ | H | S |
| X-6 | 3-Cyclopropyl | $CH_2$ | H | $CH_2CH_2$ | H | S |
| X-6 | 3-$OCH_2CH_3$ | $CH_2$ | H | $CH_2CH_2$ | H | S |
| X-6 | 3-Cyclopropyl | $CH(CH_3)$ | H | $CH(CH_3)CH_2$ | 1-$CH_3$ | S |
| X-6 | 3-Cyclopropyl | $CH_2CH_2$ | H | $CH_2CH_2CH_2$ | H | S |
| X-6 | 3-$CH_3$ | $CH_2$ | H | $CH_2CH_2$ | 2-$CH_3$ | S |
| X-6 | 3-$CH_3$ | $CH_2$ | 3-$CH_3$ | $CH_2CH_2$ | 2,2-$Cl_2$ | S |
| X-6 | 3-Cyclopropyl | $CH_2$ | H | $CH(CH_3)CH_2$ | H | S |
| X-7 | — | $CH_2$ | H | $CH_2CH_2$ | H | O |
| X-7 | 3-$CH_3$ | $CH_2$ | H | $CH_2CH_2$ | H | O |
| X-7 | 3-$CH_3$ | $CH_2$ | 3-$CH_3$ | $CH(CH_3)CH_2$ | H | O |
| X-7 | 3-$CH_3$ | $CH_2$ | H | $CH(CH_3)CH_2$ | H | O |
| X-7 | 3-$CH_3$ | $CH(CH_3)$ | H | $CH_2CH_2$ | 1-$CH_3$ | O |
| X-7 | 3-$CH_3$ | $CH_2$ | H | $CH_2CH_2$ | 2-$CH_3$ | O |
| X-7 | — | $CH_2$ | H | $CH_2CH_2$ | H | S |
| X-7 | 3-$CH_3$ | $CH_2$ | H | $CH_2CH_2$ | H | S |
| X-7 | 3-$CH_3$ | $CH_2$ | 3-$CH_3$ | $CH(CH_3)CH_2$ | H | S |
| X-7 | 3-$CH_3$ | $CH_2$ | H | $CH(CH_3)CH_2$ | H | S |
| X-7 | 3-$CH_3$ | $CH(CH_3)$ | H | $CH_2CH_2$ | 1-$CH_3$ | S |
| X-7 | 3-$CH_3$ | $CH_2$ | H | $CH_2CH_2$ | 2-$CH_3$ | S |
| X-8 | 1-$CH_3$ | $CH_2$ | H | $CH_2CH_2$ | H | O |
| X-8 | 1,3-$(CH_3)_2$ | $CH_2$ | H | $CH_2CH_2$ | H | O |
| X-8 | 1-$CH_3$, 3-Cyclopropyl | $CH_2$ | H | $CH_2CH_2$ | H | O |
| X-8 | 1-$CH_3$, 3-Cyclopropyl | $CH(CH_3)$ | H | $CH_2CH_2$ | H | O |
| X-8 | 1-$CH_3$, 3-Cyclopropyl | $CH_2$ | 3-F | $CH_2CH_2$ | H | O |
| X-8 | 1,3-$(CH_3)_2$ | $CH_2$ | H | $CH(CH_3)CH_2$ | 1-$CH_3$ | O |
| X-8 | 1,3-$(CH_3)_2$ | $CH_2$ | H | $CH_2CH_2$ | 2-$CH_3$ | O |
| X-8 | 1,4-$(CH_3)_2$ | $CH_2$ | H | $CH_2CH_2$ | H | O |
| X-8 | 1,4-$(CH_3)_2$ | $CH_2CH_2$ | H | $CH_2CH_2CH_2$ | H | O |
| X-8 | 1-$CH_3$, 3-Cyclopropyl | $CH_2$ | H | $CH_2CH_2$ | 2,2-$Cl_2$ | O |
| X-8 | 1-$CH_3$ | $CH_2$ | H | $CH_2CH_2$ | H | S |
| X-8 | 1,3-$(CH_3)_2$ | $CH_2$ | H | $CH_2CH_2$ | H | S |
| X-8 | 1-$CH_3$, 3-Cyclopropyl | $CH_2$ | H | $CH_2CH_2$ | H | S |
| X-8 | 1-$CH_3$, 3-Cyclopropyl | $CH(CH_3)$ | H | $CH_2CH_2$ | H | S |
| X-8 | 1-$CH_3$, Cyclopropyl | $CH_2$ | 3-F | $CH_2CH_2$ | H | S |
| X-8 | 1,3-$(CH_3)_2$ | $CH_2$ | H | $CH(CH_3)CH_2$ | 1-$CH_3$ | S |
| X-8 | 1,3-$(CH_3)_2$ | $CH_2$ | H | $CH_2CH_2$ | 2-$CH_3$ | S |
| X-8 | 1,4-$(CH_3)_2$ | $CH_2$ | H | $CH_2CH_2$ | H | S |
| X-8 | 1,4-$(CH_3)_2$ | $CH_2CH_2$ | H | $CH_2CH_2CH_2$ | H | S |
| X-8 | 1-$CH_3$, 3-Cyclopropyl | $CH_2$ | H | $CH_2CH_2$ | 2,2-$Cl_2$ | S |
| X-9 | 1-$CH_3$ | $CH_2$ | H | $CH_2CH_2$ | H | O |
| X-9 | 1,3-$(CH_3)_2$ | $CH_2$ | H | $CH_2CH_2$ | H | O |
| X-9 | 1,5-$(CH_3)_2$ | $CH_2$ | H | $CH_2CH_2$ | H | O |
| X-9 | 1,3-$(CH_3)_2$ | $CH_2$ | 3-F | $CH_2CH_2$ | H | O |
| X-9 | 1,5-$(CH_3)_2$ | $CH_2$ | 3-$CH_3$ | $CH_2CH_2$ | H | O |
| X-9 | 1,3-$(CH_3)_2$ | $CH_2$ | H | $CH_2CH_2$ | 1-$CH_3$ | O |
| X-9 | 1,5-$(CH_3)_2$ | $CH_2$ | H | $CH_2CH_2$ | 2-$CH_3$ | O |
| X-9 | 1,3-$(CH_3)_2$ | $CH(CH_3)$ | H | $CH(CH_3)CH_2CH_2$ | H | O |
| X-9 | 1,5-$(CH_3)_2$ | $CH_2CH_2$ | H | $CH(CH_3)CH_2$ | H | O |
| X-9 | 1-$CH_3$ | $CH_2$ | H | $CH_2CH_2$ | H | S |
| X-9 | 1,3-$(CH_3)_2$ | $CH_2$ | H | $CH_2CH_2$ | H | S |
| X-9 | 1,5-$(CH_3)_2$ | $CH_2$ | H | $CH_2CH_2$ | H | S |
| X-9 | 1,3-$(CH_3)_2$ | $CH_2$ | 3-F | $CH_2CH_2$ | H | S |
| X-9 | 1,5-$(CH_3)_2$ | $CH_2$ | 3-$CH_3$ | $CH_2CH_2$ | H | S |
| X-9 | 1,3-$(CH_3)_2$ | $CH_2$ | H | $CH_2CH_2$ | 1-$CH_3$ | S |
| X-9 | 1,5-$(CH_3)_2$ | $CH_2$ | H | $CH_2CH_2$ | 2-$CH_3$ | S |
| X-9 | 1,3-$(CH_3)_2$ | $CH_2$ | H | $CH(CH_3)CH_2CH_2$ | H | S |
| X-9 | 1,5-$(CH_3)_2$ | $CH_2CH_2$ | H | $CH(CH_3)CH_2$ | H | S |
| X-10 | 1-$CH_3$ | $CH_2$ | H | $CH_2CH_2$ | H | O |
| X-10 | 1,5-$(CH_3)_2$ | $CH_2$ | H | $CH_2CH_2$ | H | O |
| X-10 | 1-$CH_3$, 5-Cyclopropyl | $CH_2$ | H | $CH_2CH_2$ | H | O |
| X-10 | 1,4-$(CH_3)_2$ | $CH_2$ | H | $CH_2CH_2$ | H | O |
| X-10 | 1-$CH_3$, 5-Cyclopropyl | $CH_2$ | H | $CH(CH_3)CH_2$ | H | O |
| X-10 | 1-$CH_3$, 5-Cyclopropyl | $CH_2CH_2$ | H | $CH_2CH_2CH_2$ | H | O |
| X-10 | 1,5-$(CH_3)_2$ | $CH_2$ | H | $CH_2CH_2$ | 2,2-$Cl_2$ | O |

TABLE 1-continued

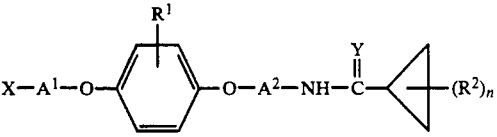

| X | Substituent on X | $A^1$ | $R^1$ | $A^2$ | $(R^2)_n$ | Y |
|---|---|---|---|---|---|---|
| X-10 | 1-CH$_3$ | CH$_2$ | H | CH$_2$CH$_2$ | H | S |
| X-10 | 1,5-(CH$_3$)$_2$ | CH$_2$ | H | CH$_2$CH$_2$ | H | S |
| X-10 | 1-CH$_3$, 5-Cyclopropyl | CH$_2$ | H | CH$_2$CH$_2$ | H | S |
| X-10 | 1,4-(CH$_3$)$_2$ | CH$_2$ | H | CH$_2$CH$_2$ | H | S |
| X-10 | 1-CH$_3$, 5-Cyclopropyl | CH$_2$ | H | CH(CH$_3$)CH$_2$ | H | S |
| X-10 | 1-CH$_3$, 5-Cyclopropyl | CH$_2$CH$_2$ | H | CH$_2$CH$_2$CH$_2$ | H | S |
| X-10 | 1,5-(CH$_3$)$_2$ | CH$_2$ | H | CH$_2$CH$_2$ | 2,2-Cl$_2$ | S |
| X-10 | 1,5-(CH$_3$)$_2$ | CH$_2$ | H | CH$_2$CH$_2$ | 1-CH$_3$ | O |
| X-10 | 1,5-(CH$_3$)$_2$ | CH$_2$ | H | CH$_2$CH$_2$ | 1-CH$_3$ | S |
| X-11 | — | CH$_2$ | H | CH$_2$CH$_2$ | H | O |
| X-11 | 3-CH$_3$ | CH$_2$ | H | CH$_2$CH$_2$ | H | O |
| X-11 | 5-CH$_3$ | CH$_2$ | H | CH$_2$CH$_2$ | H | O |
| X-11 | 3-CH$_3$ | CH$_2$ | H | CH$_2$CH$_2$ | 2-CH$_3$ | O |
| X-11 | 5-CH$_3$ | CH$_2$ | H | CH$_2$CH$_2$ | 2-CH$_3$ | O |
| X-11 | 3-CH$_3$ | CH$_2$ | 3-F | CH(CH$_3$)CH$_2$ | 1-CH$_3$ | O |
| X-11 | 5-CH$_3$ | CH$_2$ | H | CH(CH$_3$)CH$_2$ | H | O |
| X-11 | — | CH$_2$ | H | CH$_2$CH$_2$ | H | S |
| X-11 | 3-CH$_3$ | CH$_2$ | H | CH$_2$CH$_2$ | H | S |
| X-11 | 5-CH$_3$ | CH$_2$ | H | CH$_2$CH$_2$ | H | S |
| X-11 | 3-CH$_3$ | CH$_2$ | H | CH$_2$CH$_2$ | 2-CH$_3$ | S |
| X-11 | 5-CH$_3$ | CH$_2$ | H | CH$_2$CH$_2$ | 2-CH$_3$ | S |
| X-11 | 3-CH$_3$ | CH$_2$ | 3-F | CH(CH$_3$)CH$_2$ | 1-CH$_3$ | S |
| X-11 | 5-CH$_3$ | CH$_2$ | H | CH(CH$_3$)CH$_2$ | H | S |
| X-12 | — | CH$_2$ | H | CH$_2$CH$_2$ | H | O |
| X-12 | 2-CH$_3$ | CH$_2$ | H | CH$_2$CH$_2$ | H | O |
| X-12 | 2-Cyclopropyl | CH$_2$ | H | CH$_2$CH$_2$ | H | O |
| X-12 | 2-OCH$_2$CH$_3$ | CH$_2$ | H | CH$_2$CH$_2$ | H | O |
| X-12 | 2-CH$_3$ | CH$_2$ | H | CH$_2$CH$_2$ | 1-CH$_3$ | O |
| X-12 | 2-Cyclopropyl | CH$_2$ | H | CH$_2$CH$_2$ | 2-CH$_3$ | O |
| X-12 | 2-CH$_3$ | CH$_2$ | H | CH$_2$CH$_2$ | 2-CH$_3$ | O |
| X-12 | 2-Cyclopropyl | CH$_2$ | H | CH$_2$CH$_2$ | 1-CH$_3$ | O |
| X-12 | 2-CH$_3$ | CH(CH$_3$) | H | CH(CH$_3$)CH$_2$CH$_2$ | H | O |
| X-12 | 2-Cyclopropyl | CH$_2$ | H | CH$_2$CH$_2$ | 2,2-Cl$_2$ | O |
| X-12 | — | CH$_2$ | H | CH$_2$CH$_2$ | H | S |
| X-12 | 2-CH$_3$ | CH$_2$ | H | CH$_2$CH$_2$ | H | S |
| X-12 | 2-Cyclopropyl | CH$_2$ | H | CH$_2$CH$_2$ | H | S |
| X-12 | 2-OCH$_2$CH$_3$ | CH$_2$ | H | CH$_2$CH$_2$ | H | S |
| X-12 | 2-CH$_3$ | CH$_2$ | H | CH$_2$CH$_2$ | 1-CH$_3$ | S |
| X-12 | 2-Cyclopropyl | CH$_2$ | H | CH$_2$CH$_2$ | 2-CH$_3$ | S |
| X-12 | 2-CH$_3$ | CH$_2$ | H | CH$_2$CH$_2$ | 2-CH$_3$ | S |
| X-12 | 2-Cyclopropyl | CH$_2$ | H | CH$_2$CH$_2$ | 1-CH$_3$ | S |
| X-12 | 2-CH$_3$ | CH(CH$_3$) | H | CH(CH$_3$)CH$_2$CH$_2$ | H | S |
| X-12 | 2-Cyclopropyl | CH$_2$ | H | CH$_2$CH$_2$ | 2,2-Cl$_2$ | S |
| X-13 | 2-Cyclopropyl | CH$_2$ | H | CH$_2$CH$_2$ | H | O |
| X-13 | 2-CH$_3$ | CH$_2$ | H | CH$_2$CH$_2$ | H | O |
| X-13 | 2-Cyclopropyl | CH$_2$ | H | CH$_2$CH$_2$ | 1-CH$_3$ | O |
| X-13 | 2-CH$_3$ | CH$_2$ | H | CH$_2$CH$_2$ | 2-CH$_3$ | O |
| X-13 | 2-Cyclopropyl | CH$_2$ | H | CH$_2$CH$_2$ | 2-CH$_3$ | O |
| X-13 | 2-CH$_3$ | CH$_2$ | H | CH$_2$CH$_2$ | 1-CH$_3$ | O |
| X-13 | 2-OCH$_2$CH$_3$ | CH$_2$ | H | CH$_2$CH$_2$ | H | O |
| X-13 | 2-CH$_3$ | CH$_2$ | H | CH(CH$_3$)CH$_2$ | H | O |
| X-13 | 2-Cyclopropyl | CH$_2$ | H | CH(CH$_3$)CH$_2$ | 2,2-Cl$_2$ | O |
| X-13 | 2-Cyclopropyl | CH$_2$ | H | CH$_2$CH$_2$ | H | S |
| X-13 | 2-CH$_3$ | CH$_2$ | H | CH$_2$CH$_2$ | H | S |
| X-13 | 2-Cyclopropyl | CH$_2$ | H | CH$_2$CH$_2$ | 1-CH$_3$ | S |
| X-13 | 2-CH$_3$ | CH$_2$ | H | CH$_2$CH$_2$ | 2-CH$_3$ | S |
| X-13 | 2-Cyclopropyl | CH$_2$ | H | CH$_2$CH$_2$ | 2-CH$_3$ | S |
| X-13 | 2-CH$_3$ | CH$_2$ | H | CH$_2$CH$_2$ | 1-CH$_3$ | S |
| X-13 | 2-OCH$_2$CH$_3$ | CH$_2$ | H | CH$_2$CH$_2$ | H | S |
| X-13 | 2-CH$_3$ | CH$_2$ | H | CH(CH$_3$)CH$_2$ | H | S |
| X-13 | 2-Cyclopropyl | CH$_2$ | H | CH(CH$_3$)CH$_2$ | 2,2-Cl$_2$ | S |
| X-14 | — | CH$_2$ | H | CH$_2$CH$_2$ | H | O |
| X-14 | 5-CH$_3$ | CH$_2$ | H | CH$_2$CH$_2$ | H | O |
| X-14 | 5-Cyclopropyl | CH$_2$ | H | CH$_2$CH$_2$ | H | O |
| X-14 | 4-CH$_3$ | CH$_2$ | H | CH$_2$CH$_2$ | H | O |
| X-14 | 4-Cyclopropyl | CH$_2$ | H | CH$_2$CH$_2$ | H | O |
| X-14 | 5-Cl | CH$_2$ | H | CH$_2$CH$_2$CH$_2$ | H | O |
| X-14 | 4-OCH$_2$CH$_3$ | CH$_2$ | H | CH$_2$CH$_2$ | 1-CH$_3$ | O |
| X-14 | 5-Cyclopropyl | CH$_2$ | H | CH(CH$_3$)CH$_2$ | 2-CH$_3$ | O |
| X-14 | — | CH$_2$ | H | CH$_2$CH$_2$ | H | S |
| X-14 | 5-CH$_3$ | CH$_2$ | H | CH$_2$CH$_2$ | H | S |
| X-14 | 5-Cyclopropyl | CH$_2$ | H | CH$_2$CH$_2$ | H | S |
| X-14 | 4-CH$_3$ | CH$_2$ | H | CH$_2$CH$_2$ | H | S |

TABLE 1-continued

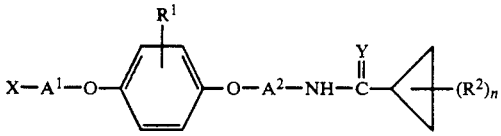

I

| X | Substituent on X | A¹ | R¹ | A² | (R²)ₙ | Y |
|---|---|---|---|---|---|---|
| X-14 | 4-Cyclopropyl | CH₂ | H | CH₂CH₂ | H | S |
| X-14 | 5-Cl | CH₂ | H | CH₂CH₂CH₂ | H | S |
| X-14 | 4-OCH₂CH₃ | CH₂ | H | CH₂CH₂ | 1-CH₃ | S |
| X-14 | 5-Cyclopropyl | CH₂ | H | CH(CH₃)CH₂ | 2-CH₃ | S |
| X-15 | — | CH₂ | H | CH₂CH₂ | H | O |
| X-15 | 2-CH₃ | CH₂ | H | CH₂CH₂ | H | O |
| X-15 | 2-Cyclopropyl | CH₂ | H | CH₂CH₂ | H | O |
| X-15 | — | CH₂ | H | CH₂CH₂ | H | S |
| X-15 | 2-CH₃ | CH₂ | H | CH₂CH₂ | H | S |
| X-15 | 2-Cyclopropyl | CH₂ | H | CH₂CH₂ | H | S |
| X-15 | 2-OCH₂CH₃ | CH₂ | H | CH₂CH₂ | H | O |
| X-15 | 2-Cl | CH₂ | H | CH₂CH₂ | H | O |
| X-15 | 2-CH₃ | CH₂ | 3-F | CH₂CH₂ | H | O |
| X-15 | 2-Cyclopropyl | CH₂CH₂ | H | CH(CH₃)CH₂ | H | O |
| X-15 | 2-CH₃ | CH₂ | H | CH₂CH₂ | 1-CH₃ | O |
| X-15 | 2-Cyclopropyl | CH₂ | H | CH₂CH₂ | 2-CH₃ | O |
| X-15 | 2-CH₃ | CH₂ | H | CH₂CH₂CH₂ | 2,2-Cl₂ | O |
| X-15 | 2-Cyclopropyl | CH(CH₃) | H | CH₂CH₂ | 2-CH₃ | O |
| X-15 | 2-OCH₂CH₃ | CH₂ | H | CH₂CH₂ | H | S |
| X-15 | 2-Cl | CH₂ | H | CH₂CH₂ | H | S |
| X-15 | 2-CH₃ | CH₂ | 3-F | CH₂CH₂ | H | S |
| X-15 | 2-Cyclopropyl | CH₂CH₂ | H | CH(CH₃)CH₂ | H | S |
| X-15 | 2-CH₃ | CH₂ | H | CH₂CH₂ | 1-CH₃ | S |
| X-15 | 2-Cyclopropyl | CH₂ | H | CH₂CH₂ | 2-CH₃ | S |
| X-15 | 2-CH₃ | CH₂ | H | CH₂CH₂CH₂ | 2,2-Cl₂ | S |
| X-15 | 2-Cyclopropyl | CH(CH₃) | H | CH₂CH₂ | 2-CH₃ | S |
| X-16 | — | CH₂ | H | CH₂CH₂ | H | O |
| X-16 | 2-CH₃ | CH₂ | H | CH₂CH₂ | H | O |
| X-16 | 2-Cyclopropyl | CH₂ | H | CH₂CH₂ | H | O |
| X-16 | 2-Cl | CH₂ | H | CH₂CH₂ | H | O |
| X-16 | 2-OCH₂CH₃ | CH₂ | H | CH₂CH₂ | H | O |
| X-16 | 2-CH₃ | CH₂ | H | CH₂CH₂ | 2-CH₃ | O |
| X-16 | 2-Cyclopropyl | CH₂ | H | CH₂CH₂ | 2-CH₃ | O |
| X-16 | 2-CH₃ | CH₂ | H | CH(CH₃)CH₂ | 2,2-Cl₂ | O |
| X-16 | 2-Cyclopropyl | CH₂ | H | CH(CH₃)CH₂ | H | O |
| X-16 | 2-CH₃ | CH₂CH₂ | 3-F | CH₂CH₂CH₂ | H | O |
| X-16 | 2-Cyclopropyl | CH₂ | H | CH(CH₃)CH₂ | 1-CH₃ | O |
| X-16 | — | CH₂ | H | CH₂CH₂ | H | S |
| X-16 | 2-CH₃ | CH₂ | H | CH₂CH₂ | H | S |
| X-16 | 2-Cyclopropyl | CH₂ | H | CH₂CH₂ | H | S |
| X-16 | 2-Cl | CH₂ | H | CH₂CH₂ | H | S |
| X-16 | 2-OCH₂CH₃ | CH₂ | H | CH₂CH₂ | H | S |
| X-16 | 2-CH₃ | CH₂ | H | CH₂CH₂ | 2-CH₃ | S |
| X-16 | 2-Cyclopropyl | CH₂ | H | CH₂CH₂ | 2-CH₃ | S |
| X-16 | 2-CH₃ | CH₂ | H | CH(CH₃)CH₂ | 2,2-Cl₂ | S |
| X-16 | 2-Cyclopropyl | CH₂ | H | CH(CH₃)CH₂ | H | S |
| X-16 | 2-CH₃ | CH₂CH₂ | 3-F | CH₂CH₂CH₂ | H | S |
| X-16 | 2-Cyclopropyl | CH₂ | H | CH(CH₃)CH₂ | 1-CH₃ | S |
| X-17 | — | CH₂ | H | CH₂CH₂ | H | O |
| X-17 | 5-Cyclopropyl | CH₂ | H | CH₂CH₂ | H | O |
| X-17 | 5-CH₃ | CH₂ | H | CH₂CH₂ | H | O |
| X-17 | 5-Cl | CH₂ | H | CH₂CH₂ | H | O |
| X-17 | 5-OCH₂CH₃ | CH₂ | H | CH₂CH₂ | H | O |
| X-17 | 4-Cyclopropyl | CH₂ | H | CH₂CH₂ | H | O |
| X-17 | 4-CH₃ | CH₂ | H | CH₂CH₂ | H | O |
| X-17 | 4-Cl | CH₂ | H | CH₂CH₂ | H | O |
| X-17 | 4-OCH₂CH₃ | CH₂ | H | CH₂CH₂ | H | O |
| X-17 | 5-Cyclopropyl | CH₂ | H | CH₂CH₂ | 1-CH₃ | O |
| X-17 | 5-CH₃ | CH(CH₃) | 3-CH₃ | CH(CH₃)CH₂ | H | O |
| X-17 | 4-CH₃ | CH₂ | H | CH₂CH₂ | 2-CH₃ | O |
| X-17 | 4-Cyclopropyl | CH₂CH₂ | H | CH₂CH₂CH₂ | H | O |
| X-17 | 5-Cyclopropyl | CH₂ | H | CH₂CH₂ | 2,2-Cl₂ | O |
| X-17 | — | CH₂ | H | CH₂CH₂ | H | S |
| X-17 | 5-Cyclopropyl | CH₂ | H | CH₂CH₂ | H | S |
| X-17 | 5-CH₃ | CH₂ | H | CH₂CH₂ | H | S |
| X-17 | 5-Cl | CH₂ | H | CH₂CH₂ | H | S |
| X-17 | 5-OCH₂CH₃ | CH₂ | H | CH₂CH₂ | H | S |
| X-17 | 4-Cyclopropyl | CH₂ | H | CH₂CH₂ | H | S |
| X-17 | 4-CH₃ | CH₂ | H | CH₂CH₂ | H | S |
| X-17 | 4-Cl | CH₂ | H | CH₂CH₂ | H | S |
| X-17 | 4-OCH₂CH₃ | CH₂ | H | CH₂CH₂ | H | S |
| X-17 | 5-Cyclopropyl | CH₂ | H | CH₂CH₂ | 1-CH₃ | S |
| X-17 | 5-CH₃ | CH(CH₃) | 3-CH₃ | CH(CH₃)CH₂ | H | S |

TABLE 1-continued

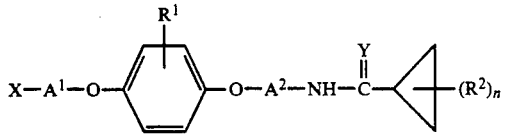

| X | Substituent on X | A¹ | R¹ | A² | (R²)ₙ | Y |
|---|---|---|---|---|---|---|
| X-17 | 4-CH₃ | CH₂ | H | CH₂CH₂ | 2-CH₃ | S |
| X-17 | 4-Cyclopropyl | CH₂CH₂ | H | CH₂CH₂CH₂ | H | S |
| X-17 | 5-Cyclopropyl | CH₂ | H | CH₂CH₂ | 2,2-Cl₂ | S |
| X-18 | 1-CH₃ | CH₂ | H | CH₂CH₂ | H | O |
| X-18 | 1,2-(CH₃)₂ | CH₂ | H | CH₂CH₂ | H | O |
| X-18 | 1,4-(CH₃)₂ | CH₂ | H | CH₂CH₂ | H | O |
| X-18 | 1,2,4-(CH₃)₃ | CH₂ | H | CH₂CH₂ | H | O |
| X-18 | 1-CH₃, 2-Cyclopropyl | CH₂ | H | CH₂CH₂ | H | O |
| X-18 | 1-CH₃, 2-Cyclopropyl | CH₂ | H | CH₂CH₂ | 1-CH₃ | O |
| X-18 | 1-CH₃, 2-Cyclopropyl | CH₂ | H | CH₂CH₂ | 2-CH₃ | O |
| X-18 | 1,2-(CH₃)₂ | CH₂ | H | CH₂CH₂ | 2,2-Cl₂ | O |
| X-18 | 1-CH₃ | CH₂CH₂ | 3-F | CH₂CH₂CH₂ | H | O |
| X-18 | 1,2,4-(CH₃)₃ | CH₂ | H | CH(CH₃)CH₂ | H | O |
| X-18 | 1,4-(CH₃)₂ | CH₂ | H | CH₂CH₂ | 2-CH₃ | O |
| X-18 | 1-CH₃, 2-Cyclopropyl | CH(CH₃) | H | CH₂CH₂ | H | O |
| X-18 | 1-CH₃, 2-Cyclopropyl | CH₂ | H | CH₂CH₂CH₂ | H | O |
| X-18 | 1-CH₃ | CH₂ | H | CH₂CH₂ | 1-CH₃ | O |
| X-18 | 1-CH₃ | CH₂ | H | CH₂CH₂ | H | S |
| X-18 | 1,2-(CH₃)₂ | CH₂ | H | CH₂CH₂ | H | S |
| X-18 | 1,4-(CH₃)₂ | CH₂ | H | CH₂CH₂ | H | S |
| X-18 | 1,2,4-(CH₃)₃ | CH₂ | H | CH₂CH₂ | H | S |
| X-18 | 1-CH₃, 2-Cyclopropyl | CH₂ | H | CH₂CH₂ | H | S |
| X-18 | 1-CH₃, 2-Cyclopropyl | CH₂ | H | CH₂CH₂ | 1-CH₃ | S |
| X-18 | 1-CH₃, 2-Cyclopropyl | CH₂ | H | CH₂CH₂ | 2-CH₃ | S |
| X-18 | 1,2-(CH₃)₂ | CH₂ | H | CH₂CH₂ | 2,2-Cl₂ | S |
| X-18 | 1-CH₃ | CH₂CH₂ | 3-F | CH₂CH₂CH₂ | H | S |
| X-18 | 1,2,4-(CH₃)₃ | CH₂ | H | CH(CH₃)CH₂ | H | S |
| X-18 | 1,4-(CH₃)₂ | CH₂ | H | CH₂CH₂ | 2-CH₃ | S |
| X-18 | 1-CH₃, 2-Cyclopropyl | CH(CH₃) | H | CH₂CH₂ | H | S |
| X-18 | 1-CH₃, 2-Cyclopropyl | CH₂ | H | CH₂CH₂CH₂ | H | S |
| X-18 | 1-CH₃ | CH₂ | H | CH₂CH₂ | 1-CH₃ | S |
| X-19 | 1-CH₃ | CH₂ | H | CH₂CH₂ | H | O |
| X-19 | 1,2-(CH₃)₂ | CH₂ | H | CH₂CH₂ | H | O |
| X-19 | 1-CH₃, 2-Cyclopropyl | CH₂ | H | CH₂CH₂ | H | O |
| X-19 | 1-CH₃ | CH₂ | H | CH₂CH₂ | 1-CH₃ | O |
| X-19 | 1,2-(CH₃)₂ | CH₂ | H | CH₂CH₂ | 1-CH₃ | O |
| X-19 | 1-CH₃, 2-Cyclopropyl | CH₂ | H | CH₂CH₂ | 1-CH₃ | O |
| X-19 | 1-CH₃ | CH₂ | H | CH₂CH₂ | 2-CH₃ | O |
| X-19 | 1,2-(CH₃)₂ | CH₂ | H | CH₂CH₂ | 2-CH₃ | O |
| X-19 | 1-CH₃, 2-Cyclopropyl | CH₂ | H | CH₂CH₂ | 2-CH₃ | O |
| X-19 | 1-CH₃ | CH₂CH₂ | H | CH(CH₃)CH₂CH₂ | H | O |
| X-19 | 1,2-(CH₃)₂ | CH(CH₃) | H | CH₂CH₂ | 2,2-Cl₂ | O |
| X-19 | 1-CH₃, 2-Cyclopropyl | CH₂ | H | CH(CH₃)CH₂ | H | O |
| X-19 | 1-CH₃ | CH₂ | H | CH₂CH₂ | H | S |
| X-19 | 1,2-(CH₃)₂ | CH₂ | H | CH₂CH₂ | H | S |
| X-19 | 1-CH₃, 2-Cyclopropyl | CH₂ | H | CH₂CH₂ | H | S |
| X-19 | 1-CH₃ | CH₂ | H | CH₂CH₂ | 1-CH₃ | S |
| X-19 | 1,2-(CH₃)₂ | CH₂ | H | CH₂CH₂ | 1-CH₃ | S |
| X-19 | 1-CH₃, 2-Cyclopropyl | CH₂ | H | CH₂CH₂ | 1-CH₃ | S |
| X-19 | 1-CH₃ | CH₂ | H | CH₂CH₂ | 2-CH₃ | S |
| X-19 | 1,2-(CH₃)₂ | CH₂ | H | CH₂CH₂ | 2-CH₃ | S |
| X-19 | 1-CH₃, 2-Cyclopropyl | CH₂ | H | CH₂CH₂ | 2-CH₃ | S |
| X-19 | 1-CH₃ | CH₂CH₂ | H | CH(CH₃)CH₂CH₂ | H | S |
| X-19 | 1,2-(CH₃)₂ | CH(CH₃) | H | CH₂CH₂ | 2,2-Cl₂ | S |
| X-19 | 1-CH₃, 2-Cyclopropyl | CH₂ | H | CH(CH₃)CH₂ | H | S |
| X-20 | 1-CH₃ | CH₂ | H | CH₂CH₂ | H | O |
| X-20 | 1,5-(CH₃)₂ | CH₂ | H | CH₂CH₂ | H | O |
| X-20 | 1-CH₃ | CH₂ | H | CH₂CH₂ | 1-CH₃ | O |
| X-20 | 1,5-(CH₃)₂ | CH₂ | H | CH₂CH₂ | 1-CH₃ | O |
| X-20 | 1-CH₃ | CH₂ | H | CH₂CH₂CH₂ | H | O |
| X-20 | 1,5-(CH₃)₂ | CH₂ | H | CH₂CH₂ | 2-CH₃ | O |
| X-20 | 1-CH₃ | CH(CH₃) | H | CH(CH₃)CH₂ | H | O |
| X-20 | 1,5-(CH₃)₂ | CH₂CH₂ | H | CH(CH₃)CH₂ | H | O |
| X-20 | 1-CH₃ | CH₂ | H | CH₂CH₂ | H | S |
| X-20 | 1,5-(CH₃)₂ | CH₂ | H | CH₂CH₂ | H | S |
| X-20 | 1-CH₃ | CH₂ | H | CH₂CH₂ | 1-CH₃ | S |
| X-20 | 1,5-(CH₃)₂ | CH₂ | H | CH₂CH₂ | 1-CH₃ | S |
| X-20 | 1-CH₃ | CH₂ | H | CH₂CH₂CH₂ | H | S |
| X-20 | 1,5-(CH₃)₂ | CH₂ | H | CH₂CH₂ | 2-CH₃ | S |
| X-20 | 1-CH₃ | CH(CH₃) | H | CH(CH₃)CH₂ | H | S |
| X-20 | 1,5-(CH₃)₂ | CH₂CH₂ | H | CH(CH₃)CH₂ | H | S |
| X-21 | — | CH₂ | H | CH₂CH₂ | H | O |
| X-21 | 4,5-Cl₂ | CH₂ | H | CH₂CH₂ | H | O |

TABLE 1-continued $$X-A^1-O-\underset{R^1}{\underset{|}{\bigcirc}}-O-A^2-NH-\overset{Y}{\underset{||}{C}}-\triangle(R^2)_n \quad \text{I}$$

| X | Substituent on X | A¹ | R¹ | A² | (R²)ₙ | Y |
|---|---|---|---|---|---|---|
| X-21 | 4,5-Br₂ | CH₂ | H | CH₂CH₂ | H | O |
| X-21 | 4,5-(CH₃)₂ | CH₂ | H | CH₂CH₂ | H | O |
| X-21 | — | CH₂ | H | CH₂CH₂CH₂ | 2,2-Cl₂ | O |
| X-21 | 4,5-Cl₂ | CH₂ | H | CH₂CH₂ | 2-CH₃ | O |
| X-21 | 4,5-Br₂ | CH(CH₃) | H | CH(CH₃)CH₂ | H | O |
| X-21 | 4,5-Cl₂ | CH₂ | 3-F | CH₂CH₂CH₂ | H | O |
| X-21 | — | CH₂ | H | CH₂CH₂ | H | S |
| X-21 | 4,5-Cl₂ | CH₂ | H | CH₂CH₂ | H | S |
| X-21 | 4,5-Br₂ | CH₂ | H | CH₂CH₂ | H | S |
| X-21 | 4,5-(CH₃)₂ | CH₂ | H | CH₂CH₂ | H | S |
| X-21 | — | CH₂ | H | CH₂CH₂CH₂ | 2,2-Cl₂ | S |
| X-21 | 4,5-Cl₂ | CH₂ | H | CH₂CH₂ | 2-CH₃ | S |
| X-21 | 4,5-Br₂ | CH(CH₃) | H | CH(CH₃)CH₂ | H | S |
| X-21 | 4,5-Cl₂ | CH₂ | 3-F | CH₂CH₂CH₂ | H | S |
| X-22 | — | CH₂ | H | CH₂CH₂ | H | O |
| X-22 | — | CH₂ | H | CH₂CH₂ | H | S |
| X-22 | 3-CH₃ | CH₂ | H | CH₂CH₂ | H | O |
| X-22 | 3-Cyclopropyl | CH₂ | H | CH₂CH₂ | H | O |
| X-22 | 3-OCH₃ | CH₂ | H | CH₂CH₂ | H | O |
| X-22 | 3-CH₃ | CH₂ | H | CH₂CH₂ | 2-CH₃ | O |
| X-22 | 3-Cyclopropyl | CH₂ | H | CH₂CH₂ | 2-CH₃ | O |
| X-22 | 3-CH₃ | CH₂ | H | CH₂CH₂ | 1-CH₃ | O |
| X-22 | 3-Cyclopropyl | CH₂ | H | CH₂CH₂ | 1-CH₃ | O |
| X-22 | 3-CH₃ | CH₂CH₂ | H | CH(CH₃)CH₂CH₂ | H | O |
| X-22 | 3-OCH₃ | CH₂ | 3-CH₃ | CH(CH₃)CH₂ | H | O |
| X-22 | 3-Cyclopropyl | CH₂ | H | CH(CH₃)CH₂ | H | O |
| X-22 | 3-CH₃ | CH₂ | H | CH₂CH₂ | H | S |
| X-22 | 3-Cyclopropyl | CH₂ | H | CH₂CH₂ | H | S |
| X-22 | 3-OCH₃ | CH₂ | H | CH₂CH₂ | H | S |
| X-22 | 3-CH₃ | CH₂ | H | CH₂CH₂ | 2-CH₃ | S |
| X-22 | 3-Cyclopropyl | CH₂ | H | CH₂CH₂ | 2-CH₃ | S |
| X-22 | 3-CH₃ | CH₂ | H | CH₂CH₂ | 1-CH₃ | S |
| X-22 | 3-Cyclopropyl | CH₂ | H | CH₂CH₂ | 1-CH₃ | S |
| X-22 | 3-CH₃ | CH₂CH₂ | H | CH(CH₃)CH₂CH₂ | H | S |
| X-22 | 3-OCH₃ | CH₂ | 3-CH₃ | CH(CH₃)CH₂ | H | S |
| X-22 | 3-Cyclopropyl | CH₂ | H | CH(CH₃)CH₂ | H | S |
| X-23 | — | CH₂ | H | CH₂CH₂ | H | O |
| X-23 | 5-CH₃ | CH₂ | H | CH₂CH₂ | H | O |
| X-23 | 5-CH₂CH₃ | CH₂ | H | CH₂CH₂ | H | O |
| X-23 | 5-CH(CH₃)₂ | CH₂ | H | CH₂CH₂ | H | O |
| X-23 | 5-Cyclopropyl | CH₂ | H | CH₂CH₂ | H | O |
| X-23 | 5-Cl | CH₂ | H | CH₂CH₂ | H | O |
| X-23 | 5-OCH₂CH₃ | CH₂ | H | CH₂CH₂ | H | O |
| X-23 | 5-CH₃ | CH₂ | H | CH₂CH₂ | 2-CH₃ | O |
| X-23 | 5-CH₃ | CH₂ | H | CH(CH₃)CH₂ | 1-CH₃ | O |
| X-23 | 5-Cyclopropyl | CH₂ | H | CH₂CH₂ | 2-CH₃ | O |
| X-23 | 5-CH(CH₃)₂ | CH₂ | H | CH₂CH₂CH₂ | H | O |
| X-23 | 5-CH₃ | CH(CH₃) | 3-CH₃ | CH(CH₃)CH₂CH₂ | H | O |
| X-23 | 5-Cyclopropyl | CH₂ | H | CH₂CH₂ | 2,2-Cl₂ | O |
| X-23 | 5-CH(CH₃)₂ | CH₂ | 3-F | CH₂CH₂ | H | O |
| X-23 | — | CH₂ | H | CH₂CH₂ | H | S |
| X-23 | 5-CH₃ | CH₂ | H | CH₂CH₂ | H | S |
| X-23 | 5-CH₂CH₂ | CH₂ | H | CH₂CH₂ | H | S |
| X-23 | 5-CH(CH₃)₂ | CH₂ | H | CH₂CH₂ | H | S |
| X-23 | 5-Cyclopropyl | CH₂ | H | CH₂CH₂ | H | S |
| X-23 | 5-Cl | CH₂ | H | CH₂CH₂ | H | S |
| X-23 | 5-OCH₂CH₂ | CH₂ | H | CH₂CH₂ | H | S |
| X-23 | 5-CH₃ | CH₂ | H | CH₂CH₂ | 2-CH₃ | S |
| X-23 | 5-CH₃ | CH₂ | H | CH(CH₃)CH₂ | 1-CH₃ | S |
| X-23 | 5-Cyclopropyl | CH₂ | H | CH₂CH₂ | 2-CH₃ | S |
| X-23 | 5-CH(CH₃)₂ | CH₂ | H | CH₂CH₂CH₂ | H | S |
| X-23 | 5-CH₃ | CH(CH₃) | 3-CH₃ | CH(CH₃)CH₂CH₂ | H | S |
| X-23 | 5-Cyclopropyl | CH₂ | H | CH₂CH₂ | 2,2-Cl₂ | S |
| X-23 | 5-CH(CH₃)₂ | CH₂ | 3-F | CH₂CH₂ | H | S |
| X-24 | — | CH₂ | H | CH₂CH₂ | H | O |
| X-24 | 3-CH₃ | CH₂ | H | CH₂CH₂ | H | O |
| X-24 | 3-Cyclopropyl | CH₂ | H | CH₂CH₂ | H | O |
| X-24 | 3-OCH₃ | CH₂ | H | CH₂CH₂ | H | O |
| X-24 | 3-CH₃ | CH₂ | H | CH₂CH₂ | 2-CH₃ | O |
| X-24 | 3-Cyclopropyl | CH₂ | H | CH₂CH₂ | 2-CH₃ | O |
| X-24 | 3-CH₃ | CH₂ | H | CH₂CH₂ | 1-CH₃ | O |
| X-24 | 3-Cyclopropyl | CH₂ | H | CH₂CH₂ | 1-CH₃ | O |
| X-24 | 3-CH₃ | CH₂CH₂ | H | CH(CH₃)CH₂CH₂ | H | O |

TABLE 1-continued

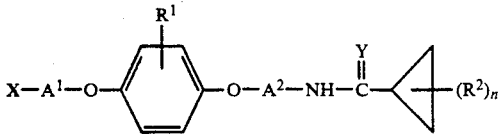

| X | Substituent on X | A¹ | R¹ | A² | (R²)$_n$ | Y |
|---|---|---|---|---|---|---|
| X-24 | 3-OCH$_3$ | CH$_2$ | 3-F | CH$_2$CH$_2$ | H | O |
| X-24 | 3-Cyclopropyl | CH$_2$ | H | CH(CH$_3$)CH$_2$ | H | O |
| X-24 | — | CH$_2$ | H | CH$_2$CH$_2$ | H | S |
| X-24 | 3-CH$_3$ | CH$_2$ | H | CH$_2$CH$_2$ | H | S |
| X-24 | 3-Cyclopropyl | CH$_2$ | H | CH$_2$CH$_2$ | H | S |
| X-24 | 3-OCH$_3$ | CH$_2$ | H | CH$_2$CH$_2$ | H | S |
| X-24 | 3-CH$_3$ | CH$_2$ | H | CH$_2$CH$_2$ | 2-CH$_3$ | S |
| X-24 | 3-Cyclopropyl | CH$_2$ | H | CH$_2$CH$_2$ | 2-CH$_3$ | S |
| X-24 | 3-CH$_3$ | CH$_2$ | H | CH$_2$CH$_2$ | 1-CH$_3$ | S |
| X-24 | 3-Cyclopropyl | CH$_2$ | H | CH$_2$CH$_2$ | 1-CH$_3$ | S |
| X-24 | 3-CH$_3$ | CH$_2$CH$_2$ | H | CH(CH$_3$)CH$_2$CH$_2$ | H | S |
| X-24 | 3-OCH$_3$ | CH$_2$ | 3-F | CH$_2$CH$_2$ | H | S |
| X-24 | 3-Cyclopropyl | CH$_2$ | H | CH(CH$_3$)CH$_2$ | H | S |
| X-25 | 5-CH$_3$ | CH$_2$ | H | CH$_2$CH$_2$ | H | O |
| X-25 | 5-CH$_2$CH$_3$ | CH$_2$ | H | CH$_2$CH$_2$ | H | O |
| X-25 | 5-CH(CH$_3$)$_2$ | CH$_2$ | H | CH$_2$CH$_2$ | H | O |
| X-25 | 5-CH$_3$ | CH$_2$ | H | CH$_2$CH$_2$ | H | S |
| X-25 | 5-CH$_2$CH$_3$ | CH$_2$ | H | CH$_2$CH$_2$ | H | S |
| X-25 | 5-CH(CH$_3$)$_2$ | CH$_2$ | H | CH$_2$CH$_2$ | H | S |
| X-25 | 5-Cyclopropyl | CH$_2$ | H | CH$_2$CH$_2$ | H | O |
| X-25 | 5-OCH$_3$ | CH$_2$ | H | CH$_2$CH$_2$ | H | O |
| X-25 | 5-OCH$_2$CH$_3$ | CH$_2$ | H | CH$_2$CH$_2$ | H | O |
| X-25 | 5-Cyclopropyl | CH$_2$ | H | CH$_2$CH$_2$ | 2-CH$_3$ | O |
| X-25 | 5-CH$_3$ | CH$_2$ | H | CH$_2$CH$_2$ | 2-CH$_3$ | O |
| X-25 | 5-CH(CH$_3$)$_2$ | CH$_2$ | H | CH$_2$CH$_2$ | 2-CH$_3$ | O |
| X-25 | 5-Cyclopropyl | CH$_2$ | H | CH$_2$CH$_2$ | 1-CH$_3$ | O |
| X-25 | 5-CH$_3$ | CH$_2$ | H | CH(CH$_3$)CH$_2$ | H | O |
| X-25 | 5-Cyclopropyl | CH$_2$ | 3-F | CH(CH$_3$)CH$_2$ | H | O |
| X-25 | 5-OCH$_2$CH$_3$ | CH$_2$ | H | CH(CH$_3$)CH$_2$ | H | O |
| X-25 | 5-Cyclopropyl | CH(CH$_3$) | 3-CH$_3$ | CH(CH$_3$)CH$_2$ | H | O |
| X-25 | 5-CH(CH$_3$)$_2$ | CH$_2$ | H | CH$_2$CH$_2$ | 2,2-Cl$_2$ | O |
| X-25 | 5-CH$_3$ | CH$_2$ | H | CH$_2$CH$_2$ | 1-CH$_3$ | O |
| X-25 | 5-Cyclopropyl | CH$_2$CH$_2$ | H | CH(CH$_3$)CH$_2$CH$_2$ | 2,2-Cl$_2$ | O |
| X-25 | 5-Cyclopropyl | CH$_2$ | H | CH$_2$CH$_2$CH$_2$ | H | O |
| X-25 | 5-Cyclopropyl | CH$_2$ | H | CH$_2$CH$_2$ | H | S |
| X-25 | 5-OCH$_3$ | CH$_2$ | H | CH$_2$CH$_2$ | H | S |
| X-25 | 5-OCH$_2$CH$_3$ | CH$_2$ | H | CH$_2$CH$_2$ | H | S |
| X-25 | 5-Cyclopropyl | CH$_2$ | H | CH$_2$CH$_2$ | 2-CH$_3$ | S |
| X-25 | 5-CH$_3$ | CH$_2$ | H | CH$_2$CH$_2$ | 2-CH$_3$ | S |
| X-25 | 5-CH(CH$_3$)$_2$ | CH$_2$ | H | CH$_2$CH$_2$ | 2-CH$_3$ | S |
| X-25 | 5-Cyclopropyl | CH$_2$ | H | CH$_2$CH$_2$ | 1-CH$_3$ | S |
| X-25 | 5-CH$_3$ | CH$_2$ | H | CH(CH$_3$)CH$_2$ | H | S |
| X-25 | 5-Cyclopropyl | CH$_2$ | 3-F | CH(CH$_3$)CH$_2$ | H | S |
| X-25 | 5-OCH$_2$CH$_3$ | CH$_2$ | H | CH(CH$_3$)CH$_2$ | H | S |
| X-25 | 5-Cyclopropyl | CH(CH$_3$) | 3-CH$_3$ | CH(CH$_3$)CH$_2$ | H | S |
| X-25 | 5-CH(CH$_3$)$_2$ | CH$_2$ | H | CH$_2$CH$_2$ | 2,2-Cl$_2$ | S |
| X-25 | 5-CH$_3$ | CH$_2$ | H | CH$_2$CH$_2$ | 1-CH$_3$ | S |
| X-25 | 5-Cyclopropyl | CH$_2$CH$_2$ | H | CH(CH$_3$)CH$_2$CH$_2$ | 2,2-Cl$_2$ | S |
| X-25 | 5-Cyclopropyl | CH$_2$ | H | CH$_2$CH$_2$CH$_2$ | H | S |
| X-26 | 1-CH$_3$ | CH$_2$ | H | CH$_2$CH$_2$ | H | O |
| X-26 | 1,5-(CH$_3$)$_2$ | CH$_2$ | H | CH$_2$CH$_2$ | H | O |
| X-26 | 1-CH$_3$, 5-Cyclopropyl | CH$_2$ | H | CH$_2$CH$_2$ | H | O |
| X-26 | 1-CH$_3$ | CH$_2$ | H | CH(CH$_3$)CH$_2$ | H | O |
| X-26 | 1,5-(CH$_3$)$_2$ | CH$_2$ | H | CH$_2$CH$_2$CH$_2$ | 2-CH$_3$ | O |
| X-26 | 1-CH$_3$, 5-Cyclopropyl | CH$_2$ | H | CH$_2$CH$_2$ | 1-CH$_3$ | O |
| X-26 | 1-CH$_3$ | CH(CH$_3$) | H | CH$_2$CH$_2$CH$_2$ | H | O |
| X-26 | 1-CH$_3$, 5-Cyclopropyl | CH$_2$CH$_2$ | 3-F | CH$_2$CH$_2$ | 2,2-Cl$_2$ | O |
| X-26 | 1-CH$_3$ | CH$_2$ | H | CH$_2$CH$_2$ | H | S |
| X-26 | 1,5-(CH$_3$)$_2$ | CH$_2$ | H | CH$_2$CH$_2$ | H | S |
| X-26 | 1-CH$_3$, 5-Cyclopropyl | CH$_2$ | H | CH$_2$CH$_2$ | H | S |
| X-26 | 1-CH$_3$ | CH$_2$ | H | CH(CH$_3$)CH$_2$ | H | S |
| X-26 | 1,5-(CH$_3$)$_2$ | CH$_2$ | H | CH$_2$CH$_2$CH$_2$ | 2-CH$_3$ | S |
| X-26 | 1-CH$_3$, 5-Cyclopropyl | CH$_2$ | H | CH$_2$CH$_2$ | 1-CH$_3$ | S |
| X-26 | 1-CH$_3$ | CH(CH$_3$) | H | CH$_2$CH$_2$CH$_2$ | H | S |
| X-26 | 1-CH$_3$, 5-Cyclopropyl | CH$_2$CH$_2$ | 3-F | CH$_2$CH$_2$ | 2,2-Cl$_2$ | S |
| X-27 | — | CH$_2$ | H | CH$_2$CH$_2$ | H | O |
| X-27 | 2-Cl | CH$_2$ | H | CH$_2$CH$_2$ | H | O |
| X-27 | 2,5-(CH$_3$)$_2$ | CH$_2$ | H | CH$_2$CH$_2$ | H | O |
| X-27 | — | CH$_2$ | H | CH$_2$CH$_2$ | 2-CH$_3$ | O |
| X-27 | 2-Cl | CH$_2$ | H | CH$_2$CH$_2$ | 2-CH$_3$ | O |
| X-27 | 2,5-(CH$_3$)$_2$ | CH$_2$ | H | CH$_2$CH$_2$ | 2-CH$_3$ | O |
| X-27 | — | CH(CH$_3$) | 3-F | CH(CH$_3$)CH$_2$CH$_2$ | H | O |
| X-27 | — | CH$_2$ | H | CH$_2$CH$_2$ | 1-CH$_3$ | O |

TABLE 1-continued

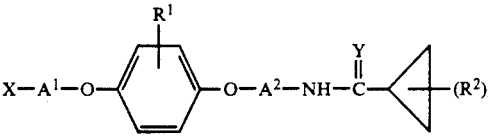

| X | Substituent on X | A¹ | R¹ | A² | (R²)ₙ | Y |
|---|---|---|---|---|---|---|
| X-27 | — | CH₂ | H | CH₂CH₂ | H | S |
| X-27 | 2-Cl | CH₂ | H | CH₂CH₂ | H | S |
| X-27 | 2,5-(CH₃)₂ | CH₂ | H | CH₂CH₂ | H | S |
| X-27 | — | CH₂ | H | CH₂CH₂ | 2-CH₃ | S |
| X-27 | 2-Cl | CH₂ | H | CH₂CH₂ | 2-CH₃ | S |
| X-27 | 2,5-(CH₃)₂ | CH₂ | H | CH₂CH₂ | 2-CH₃ | S |
| X-27 | — | CH(CH₃) | 3-F | CH(CH₃)CH₂CH₂ | H | S |
| X-27 | — | CH₂ | H | CH₂CH₂ | 1-CH₃ | S |
| X-28 | 1-CH₃ | CH₂ | H | CH₂CH₂ | H | O |
| X-28 | 1,5-(CH₃)₂ | CH₂ | H | CH₂CH₂ | H | O |
| X-28 | 1-CH₃, 5-Cyclopropyl | CH₂ | H | CH₂CH₂ | H | O |
| X-28 | 1-CH₃ | CH₂ | H | CH₂CH₂ | 1-CH₃ | O |
| X-28 | 1,5-(CH₃)₂ | CH₂ | H | CH₂CH₂ | 1-CH₃ | O |
| X-28 | 1-CH₃, 5-Cyclopropyl | CH₂ | H | CH₂CH₂ | 2-CH₃ | O |
| X-28 | 1-CH₃ | CH₂ | H | CH(CH₃)CH₂ | 2,2-Cl₂ | O |
| X-28 | 1-CH₃ | CH₂ | H | CH₂CH₂ | H | S |
| X-28 | 1,5-(CH₃)₂ | CH₂ | H | CH₂CH₂ | H | S |
| X-28 | 1-CH₃, 5-Cyclopropyl | CH₂ | H | CH₂CH₂ | H | S |
| X-28 | 1-CH₃ | CH₂ | H | CH₂CH₂ | 1-CH₃ | S |
| X-28 | 1,5-(CH₃)₂ | CH₂ | H | CH₂CH₂ | 1-CH₃ | S |
| X-28 | 1-CH₃, 5-Cyclopropyl | CH₂ | H | CH₂CH₂ | 2-CH₃ | S |
| X-28 | 1-CH₃ | CH₂ | H | CH(CH₃)CH₂ | 2,2-Cl₂ | S |
| X-28 | 1,5-(CH₃)₂ | CH₂ | H | CH₂CH₂ | 2-CH₃ | O |
| X-28 | 1-CH₃, 5-Cyclopropyl | CH₂ | H | CH₂CH₂ | 1-CH₃ | O |
| X-28 | 1-CH₃ | CH₂CH₂ | H | CH₂CH₂CH₂ | H | O |
| X-28 | 1,5-(CH₃)₂ | CH₂ | H | CH₂CH₂ | 2-CH₃ | S |
| X-28 | 1-CH₃, 5-Cyclopropyl | CH₂ | H | CH₂CH₂ | 1-CH₃ | S |
| X-28 | 1-CH₃ | CH₂CH₂ | H | CH₂CH₂CH₂ | H | S |
| X-29 | 1-CH₃ | CH₂ | H | CH₂CH₂ | H | O |
| X-29 | 1,3-(CH₃)₂ | CH₂ | H | CH₂CH₂ | H | O |
| X-29 | 1-CH₃, 3-Cyclopropyl | CH₂ | H | CH₂CH₂ | H | O |
| X-29 | 1-CH₃ | CH₂ | H | CH₂CH₂ | 2-CH₃ | O |
| X-29 | 1,3-(CH₃)₂ | CH₂ | H | CH₂CH₂ | 2-CH₃ | O |
| X-29 | 1-CH₃, 3-Cyclopropyl | CH₂ | H | CH₂CH₂ | 2-CH₃ | O |
| X-29 | 1-CH₃ | CH₂ | H | CH₂CH₂CH₂ | 1-CH₃ | O |
| X-29 | 1-CH₃ | CH₂ | H | CH₂CH₂ | H | S |
| X-29 | 1,3-(CH₃)₂ | CH₂ | H | CH₂CH₂ | H | S |
| X-29 | 1-CH₃, 3-Cyclopropyl | CH₂ | H | CH₂CH₂ | H | S |
| X-29 | 1-CH₃ | CH₂ | H | CH₂CH₂ | 2-CH₃ | S |
| X-29 | 1,3-(CH₃)₂ | CH₂ | H | CH₂CH₂ | 2-CH₃ | S |
| X-29 | 1-CH₃, 3-Cyclopropyl | CH₂ | H | CH₂CH₂ | 2-CH₃ | S |
| X-29 | 1-CH₃ | CH₂ | H | CH₂CH₂CH₂ | 1-CH₃ | S |
| X-30 | — | CH₂ | H | CH₂CH₂ | H | O |
| X-30 | 3,5-(CH₃)₂ | CH₂ | H | CH₂CH₂ | H | O |
| X-30 | — | CH₂ | H | CH₂CH₂ | 2-CH₃ | O |
| X-30 | 3,5-(CH₃)₂ | CH₂ | H | CH₂CH₂ | 1-CH₃ | O |
| X-30 | — | CH₂ | 3-F | CH₂(CH₃)CH₂ | H | O |
| X-30 | 3,5-(CH₃)₂ | CH₂(CH₃) | H | CH₂CH₂ | H | O |
| X-30 | — | CH₂ | H | CH₂CH₂ | 2,2-Cl₂ | O |
| X-30 | 3,5-(CH₃)₂ | CH₂CH₂ | H | CH₂CH₂CH₂ | H | O |
| X-30 | — | CH₂ | H | CH₂CH₂ | H | S |
| X-30 | 3,5-(CH₃)₂ | CH₂ | H | CH₂CH₂ | H | S |
| X-30 | — | CH₂ | H | CH₂CH₂ | 2-CH₃ | S |
| X-30 | 3,5-(CH₃)₂ | CH₂ | H | CH₂CH₂ | 1-CH₃ | S |
| X-30 | — | CH₂ | 3-F | CH₂(CH₃)CH₂ | H | S |
| X-30 | 3,5-(CH₃)₂ | CH₂(CH₃) | H | CH₂CH₂ | H | S |
| X-30 | — | CH₂ | H | CH₂CH₂ | 2,2-Cl₂ | S |
| X-30 | 3,5-(CH₃)₂ | CH₂CH₂ | H | CH₂CH₂CH₂ | H | S |
| X-31 | — | CH₂CH₂ | H | CH₂CH₂ | H | O |
| X-31 | 4-Cl | CH₂CH₂ | H | CH₂CH₂ | H | O |
| X-31 | 3,5-(CH₃)₂ | CH₂CH₂ | H | CH₂CH₂ | H | O |
| X-31 | 4-Cl | CH₂CH₂CH₂ | H | CH₂CH₂ | H | O |
| X-31 | 4-Cl | CH₂CH₂ | H | CH(CH₃)CH₂ | 2-CH₂ | O |
| X-31 | — | CH₂CH₂ | H | CH₂CH₂CH₂ | 2,2-Cl₂ | O |
| X-31 | — | CH₂CH₂ | H | CH₂CH₂ | H | S |
| X-31 | 4-Cl | CH₂CH₂ | H | CH₂CH₂ | H | S |
| X-31 | 3,5-(CH₃)₂ | CH₂CH₂ | H | CH₂CH₂ | H | S |
| X-31 | 4-Cl | CH₂CH₂CH₂ | H | CH₂CH₂ | H | S |
| X-31 | 4-Cl | CH₂CH₂ | H | CH(CH₃)CH₂ | 2-CH₃ | S |
| X-31 | — | CH₂CH₂ | H | CH₂CH₂CH₂ | 2,2-Cl₂ | S |
| X-32 | — | CH₂CH₂ | H | CH₂CH₂ | H | O |
| X-32 | — | CH₂CH₂ | H | CH(CH₃)CH₂ | H | O |
| X-32 | 3-CH₃ | CH₂CH₂ | H | CH₂CH₂ | H | O |

TABLE 1-continued $$X-A^1-O-\underset{R^1}{\underset{|}{\bigcirc}}-O-A^2-NH-\underset{\underset{C}{\|}}{\overset{Y}{C}}-\triangle(R^2)_n \quad I$$

| X | Substituent on X | A¹ | R¹ | A² | (R²)ₙ | Y |
|---|---|---|---|---|---|---|
| X-32 | 5-CH₃ | CH₂CH₂ | H | CH₂CH₂ | H | O |
| X-32 | — | CH₂CH₂CH₂ | H | CH₂CH₂CH₂ | 2-CH₃ | O |
| X-32 | 5-CH₃ | CH₂CH₂ | 3-F | CH₂CH₂ | 1-CH₃ | O |
| X-32 | — | CH₂CH₂ | H | CH₂CH₂ | H | S |
| X-32 | — | CH₂CH₂ | H | CH(CH₃)CH₂ | H | S |
| X-32 | 3-CH₃ | CH₂CH₂ | H | CH₂CH₂ | H | S |
| X-32 | 5-CH₃ | CH₂CH₂ | H | CH₂CH₂ | H | S |
| X-32 | — | CH₂CH₂CH₂ | H | CH₂CH₂CH₂ | 2-CH₃ | S |
| X-32 | 5-CH₃ | CH₂CH₂ | 3-F | CH₂CH₂ | 1-CH₃ | S |

For synthesizing the cyclopropane(thio)carboxamides I, phenols of the general formula VIII and primary amines of the general formula I are used as intermediates. The substituents R¹, R² and A² in VIII and R¹, A¹, A² and X in X have the general and special meanings given above.

The compounds of the formula I are suitable for effectively combating pests such as insects, arachnids and nematodes. They may be used as pesticides in crop protection and in the hygiene, stores protection and veterinary sector.

Examples of injurious insects belonging to the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantrai monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana,, Trichoplusia ni* and *Zeiraphera canadensis*.

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta crysocephala, Phyllophaga sp., Phyllopertha horticola, Phyllotreta nemorum, Phyllotreta striolata, Popillia japonica, Sitona lineatus* and *Sitophilus granaria*.

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucila caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*.

Examples from the Thysanoptera order are *Frankliniella fusca, Franliniella occidentalis, Frankliniella tritici, Scirtothrips citri, Thrips oryzae, Thrips palmi* and *Trhips tabaci*.

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta*.

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor*.

Examples from the Homoptera order are *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosi-*

*phum maidis, Sappaphis mala, Sappaphis mali, Schizaphis graminum, Schizoneura lanuginosa, Trialeurodes vaporariorum* and *Viteus vitifolii.*

Examples from the Isoptera order are *Calotermes flavicollis, Leucotermes flavipes, Reticulitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

Examples from the Acarina order are *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsoneumu latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

Examples from the nematodes class are root-knot nematodes, e.g., *Meloidogyne hapla, Meloidogyne incognita* and *Meloidogyne javanica,* cyst-forming nematodes, e.g., *Globodera rostochiensis, Heterodera avenae, Hetrodera glycinae, Heterodera schachtii* and *Heterodera trifolii,* and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coat-tar oils, and oils of vegetable or animal origin, aliphatis, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting gent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

The formulations generally contain from 0.01 to 95, and preferably from 0.1 to 90, wt% of active ingredient. The active ingredients are used in a purity of from 90 to 100, and preferably from 95 to 100, % (based on the NMR spectrum).

Examples of formulations are given below.

I. 5 parts by weight of compound no. 2.06 is intimately mixed with 95 parts by weight of particulate kaolin. A dust is obtained containing 5% by weight of the active ingredient.

II. 30 parts by weight of compound no. 2.11 is intimately mixed with a mixture consisting of 92 parts by weight of powdered silica gel and 8 parts by weight of paraffin oil which has been sprayed onto the surface of this silica gel. A formulation of the active ingredient is obtained having good adherence (active ingredient content: 23 wt%).

III. 10 parts by weight of compound no. 2.08 is dissolved in a mixture consisting of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil (active ingredient content: 9 wt%).

IV. 20 parts by weight of compound no. 2.14 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil (active ingredient content: 16 wt%).

V. 80 parts by weight of compound no. 2.03 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill (active ingredient content: 80 wt%).

VI. 90 parts by weight of compound no. 2.10 is mixed with 10 parts by weight of N-methyl-alpha-pyrrolidone. A mixture is obtained which is suitable for application in the form of very fine drops (active ingredient content: 90 wt%).

VII. 20 parts by weight of compound no. 2.04 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

VIII. 20 parts by weight of compound no. 2.15 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The active ingredient concentrations in the finished formulations may vary over a wide range. Generally, they are from 0.0001 to 10, and preferably from 0.01 to 1, %.

The active ingredients may also successfully be used in the ultra-low-volume (ULV) method, where it is possible to apply formulations containing more than 95 wt% of active ingredient, or even the active ingredient without additives.

In the open, the amount of active ingredient applied is for example from 0.01 to 10, particularly from 0.1 to 1, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

PREPARATION EXAMPLES

The directions given below for the manufacture of the compounds were used, after modifications to the starting materials, to produce further compounds according to the invention. These compounds and their physical data are given in the tables below.

A. Preparation of intermediates of the general formula VIII

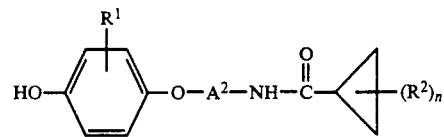

20 ml (~1 eq) of concentrated HCl was added to a solution of 63.7 g (0.23 mol) of cyclopropanecarboxylic acid-N-2-(4-tert-butoxyphenoxy)-ethylamide in 1000 ml of ethanol/water (10/1), and the mixture was refluxed for 2 hours. The solvent was evaporated off, water was added to the residue, the pH of the mixture was adjusted to 7, and the precipitate was suction filtered.

Yield: 46.4 g (91%) of white crystals, m.p. 115° C.

EXAMPLE 1

5-(4-Cyclopropylcarbonylaminoethoxyphenoxy)-methyl-3-isopropylisoxazole (Compound no. 2.02 in Table 2)

At room temperature, a solution of 9.7 g (44 mmol) of the compound prepared in A.1 in 70 ml of DMF was added dropwise to a suspension of 1.3 g (1 eq) of NaH (80% strength dispersion in mineral oil) in 60 ml of DMF; the mixture was heated at 80° C. for 1 hour. After a solution of 7.0 g (44 mmol) of 5-chloromethyl-3-isopropylisoxazole in 50 ml of DMF had been added, the mixture was heated at 120° C. for 6 hours, and then the solvent was evaporated off and the residue was taken up in ethyl acetate and washed with water. Evaporation of the solvent and recrystallization from ethanol of the solid obtained gave 8.7 g (57%) of the desired phenol ether; m.p. 76°–80° C.

EXAMPLE 2

5-(4-Cyclopropylcarbonylaminoethoxyphenoxy)-methyl-2-cyclopropyl-1,3-4-thiadiazole (Compound no. 2.05 in Table 2)

Reaction of 9.7 g (44 mole) of VII a and 7.6 g (44 mmol) of 5-chloromethyl-2-cyclopropyl-1,3,4-thiadiazole analogously to Synthesis Example 2 gave, after recrystallization of the crude product from ethanol, 7.9 g (50%) of the desired phenol ether; m.p. 105°–112° C.

EXAMPLE 3

5-(4-Cyclopropylthiocarbonylaminoethyoxyphenoxy)-methyl-3-isopropylisoxazole (Compound no. 2.10 in Table 2)

A suspension of 5.85 g (17 mmol) of compound no. 2.03 and 6.9 g (17 mmol) of Lawesson's reagent in 100 ml of toluene was heated at 80° C. for 1 hour. The solvent was removed and the crude product was prepurified chromatographically (silica gel, cyclohexane/ethyl acetate=1/1). Recrystallization of the product from cyclohexane/ethyl acetate gave 2.7 g (44%) of the desired thioamide; m.p. 95°–102° C.

EXAMPLE 4

5-(4-Cyclopropylthiocarbonylaminoethoxyphenoxy)-methyl-2-cyclopropyl-1,3,4-thiadiozole (Compound no. 2.13 in Table 2)

A suspension of 4.3 g (12 mmol) of compound no. 2.05 and 5.6 g (13.8 mmol) of Lawesson's reagent in 100 ml of toluene was heated at 80° C. for 1 hour. After removal of the solvent and chromatographic purification of the crude product (silica gel, cyclohexane/ethyl acetate=1/1), there was obtained 3.9 g (87%) of the desired thioamide, m.p. 114°-116° C.

TABLE 2

$$X-A^1-O-\underset{}{\bigcirc}-O-CH_2CH_2-NH-\overset{Y}{\underset{\|}{C}}-\triangle$$

| No. | X* | $A^1$ | Y | Physical data (mp. (°C.)) |
|---|---|---|---|---|
| 2.01 | H₃C-isoxazoline | CH₂ | O | 108-115 |
| 2.02 | iP-isoxazoline | CH₂ | O | 76-80 |
| 2.03 | cP-isoxazoline | CH₂ | O | 119-122 |
| 2.04 | H₃C-thiadiazole | CH₂ | O | 134-137 |
| 2.05 | cP-thiadiazole | CH₂ | O | 105-112 |
| 2.06 | CH₃CH₂O-thiadiazole | CH₂ | O | 82-93 |
| 2.07 | H₃C-oxadiazole | CH₂ | O | 106-109 |
| 2.08 | iP-oxadiazole | CH₂ | O | 82-84 |
| 2.09 | cP-oxadiazole | CH₂ | O | 88-91 |
| 2.10 | iP-isoxazoline | CH₂ | S | 95-102 |
| 2.11 | cP-isoxazoline | CH₂ | S | 118-120 |
| 2.12 | H₃C-thiadiazole | CH₂ | S | 95-105 |
| 2.13 | cP-thiadiazole | CH₂ | S | 114-116 |
| 2.14 | H₃C-oxadiazole | CH₂ | S | 130-133 |
| 2.15 | cP-oxadiazole | CH₂ | S | 82-87 |

*cP = cyclopropyl; iP = isopropyl

USE EXAMPLES

The insecticidal action of compounds of the general formula I is demonstrated by the following experiments:
The active ingredients were formulated
a) as a 0.1% strength solution in acetone, or
b) as a 10% strength emulsion in a mixture of 70 wt% of cyclohexanol, 20 wt% of Nekanil ® LN (Lutensol ® AP6, a spreader-sticker with an emulsifying and dispersing action based on ethoxylated alkylphenols) and 10 wt% of Emulphor ® EL (Emulan ® EL, an emulsifier based on ethoxylated fatty alcohols)
and diluted to the desired concentration with acetone in the case of a) and with water in the case of b).

Upon conclusion of the experiments the lowest concentration was determined at which the compounds—compared with the untreated controls—caused 80 to 100% inhibition or mortality (action threshold or minimum concentration).

A) *Prodenia litura*; breeding experiment

The bottoms of vessels were wetted with acetonic solutions of the active ingredients. After the solvent had evaporated, 5 caterpillars in the 4th larval stage were introduced.

The kill rate was determined after 4 hours.

In this test, compounds 2.01, 2.04, 2.09, 2.13 and 2.15 had action thresholds of from 0.0001 to 0.0004 ppm.

B) *Prodenia litura*; morphogenesis 5 caterpillars of the L3 development stage (10-12 mm) were placed on a standard nutrient medium (3.1 liters of water, 80 g of agar, 137 g of brewer's yeast, 515 g of cornflour, 130 g of wheat germ, and conventional additives and vitamins (20 g of Wessons salt, 5 g of Nipagin, 5 g of sorbitol, 10 g of cellulose powder, 18 g of ascorbic acid, 1 g of Lutavit ® blend (vitamin) and 5 ml of alcoholic biotin solution)) which had previously been wetted with aqueous solutions of the active ingredients. Monitoring was continued until pupation in a control experiment without active ingredients. Any changes in development occurring during the experiment were assessed in comparison with normal development.

In this test, compounds 2.01, 2.04, 2.09, 2.13 and 2.15 had action thresholds of from 0.001 to 0.004 ppm.

We claim:
1. A cyclopropane(thio)carboxamide of the formula I

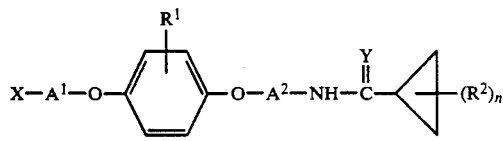

where
n is 0, 1 or 2, it being possible for the $R^1$ radicals to be different when n is 2;
$A^1$ is methylene, ethylene or propylene, it being possible for these groups to carry one or two $C_1$-$C_3$-alkyl groups;
$A^2$ is ethylene or propylene, it being possible for these groups to carry one or two $C_1$-$C_3$-alkyl groups;
$R^1$ is hydrogen, halogen or $C_1$-$C_6$-alkyl;
$R^2$ is halogen or $C_1$-$C_3$-alkyl;
X is a 5-membered heteroaromatic radical selected from the group consisting of isoxazole, thiadiazole and oxadiazole, it being possible for these 5-membered heteroaromatic rings to carry on their carbon atoms from one to three of the following: nitro, cyano, $C_1$-$C_6$-alkyl, $C_1$-$C_4$-haloalkyl, $C_1$-$C_6$-alkoxy, $C_1$-$C_4$-haloalkoxy, $C_1$-$C_4$-alkylthio, $C_1$-$C_4$-haloalkythio, $C_1$-$C_4$-alkoxy-$C_1$-$C_4$-alkyl, $C_3$-$C_8$-cycloalkyl, $C_2$-$C_8$-alkenyl, $C_2$-$C_8$-alkynyl, aryl or aryl-$C_1$-$C_{10}$-alkyl, it being possible for the aromatic radicals in turn to carry from one to five halogens and/or from one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;
Y is oxygen or sulfur.

2. A pesticide composition containing an effective amount of a compound of the formula I as defined in claim 1 and inert additives.

3. A method for controlling pests, which comprises treating the pests and/or their habitat with an effective amount of a compound of the formula I as defined in claim 1.

4. A compound of formula I as defined in claim 1, wherein
X is 5-cyclopropyl-oxa-3,4-diazol-2-yl;
$A^1$ is $CH_2$;
$R^1$ is H;
$A^2$ $CH_2CH_2$;
Y is S; and
n is 0.

5. A pesticidal composition containing an effective amount of the compound of claim 4 and inert additives.

6. A method for controlling pests which comprises: treating the pests and/or their habitat with an effective amount of the compound of claim 4.

* * * * *